(12) United States Patent
Wu

(10) Patent No.: US 12,139,539 B2
(45) Date of Patent: Nov. 12, 2024

(54) MIC ANTIBODIES AND BINDING AGENTS AND METHODS OF USING THE SAME

(71) Applicant: Cancure, LLC, Shoreline, WA (US)

(72) Inventor: Jennifer Wu, Wilmette, IL (US)

(73) Assignee: CanCure, LLC, Shoreline, WA (US)

( * ) Notice: Subject to any disclaimer, the term of this patent is extended or adjusted under 35 U.S.C. 154(b) by 0 days.

(21) Appl. No.: 18/049,434

(22) Filed: Oct. 25, 2022

(65) Prior Publication Data

US 2023/0235065 A1 Jul. 27, 2023

Related U.S. Application Data

(63) Continuation of application No. PCT/US2021/040445, filed on Jul. 6, 2021.

(60) Provisional application No. 63/049,012, filed on Jul. 7, 2020.

(51) Int. Cl.
| | | |
|---|---|---|
| *C07K 16/30* | (2006.01) | |
| *A61P 35/00* | (2006.01) | |
| *C07K 16/28* | (2006.01) | |
| *C07K 16/44* | (2006.01) | |
| *C12N 15/63* | (2006.01) | |

(52) U.S. Cl.
CPC .......... *C07K 16/2833* (2013.01); *A61P 35/00* (2018.01); *C12N 15/63* (2013.01); *C07K 2317/565* (2013.01)

(58) Field of Classification Search
CPC .......................... C07K 16/30; A61K 39/39558
See application file for complete search history.

(56) References Cited

U.S. PATENT DOCUMENTS

| | | | |
|---|---|---|---|
| 7,317,091 B2 | 1/2008 | Lazar et al. | |
| 8,969,526 B2 | 3/2015 | Baehner et al. | |
| 9,803,017 B2 | 10/2017 | Wu | |
| 10,577,416 B2 | 3/2020 | Blery et al. | |
| 10,793,633 B2 | 10/2020 | Wucherpfennig et al. | |
| 11,242,393 B2 | 2/2022 | Kuhne et al. | |
| 11,857,571 B2 | 1/2024 | Sentman et al. | |
| 2016/0368991 A1 | 12/2016 | Wu | |
| 2018/0237526 A1 | 8/2018 | Wu | |
| 2020/0055939 A1 | 2/2020 | Lombana et al. | |
| 2022/0002382 A1 | 1/2022 | Dranoff et al. | |

FOREIGN PATENT DOCUMENTS

| | | | |
|---|---|---|---|
| WO | 2008036981 A1 | 3/2008 | |
| WO | 2012091756 A1 | 7/2012 | |
| WO | 2014144791 A3 | 11/2014 | |
| WO | 2015003114 A1 | 1/2015 | |
| WO | 2015179627 A1 | 11/2015 | |
| WO | 2017096374 A1 | 6/2017 | |
| WO | 2018073648 A1 | 4/2018 | |
| WO | 2018081648 A2 | 5/2018 | |
| WO | 2019004550 A1 | 1/2019 | |
| WO | 2020028428 A2 | 2/2020 | |
| WO | 2020086776 A1 | 4/2020 | |
| WO | 2021041238 A1 | 3/2021 | |
| WO | 2023076883 A1 | 5/2023 | |

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Caldas et al. "Humanization of the anti-CD18 antibody 6.7: an unexpected effect of a framework residue in binding to antigen", Molecular Immunology, vol. 39, No. 5, pp. 941-652 (2003).
Du et al. "Molecular basis of recognition of human osteopontin by 23C3, a potential therapeutic antibody for treatment of rheumatoid arthritis", Journal of Molecular Biology, vol. 382, No. 4, pp. 835-842 (2008).
International Search Report issued in PCT/US2021/040445 dated Oct. 28, 2021, 14 pages.
Panka et al., "Variable Region Framework Differences Result in Decreased or Increased Affinity of Variant Anti-Digoxin Antibodies", Proceedings of the National Academy of Sciences, vol. 85, No. 9, pp. 3080-3084 (1988).
Xiang et al., "Modification in framework region I results in a decreased affinity of chimeric anti-TAG72 antibody", Molecular Immunology, vol. 28, No. 1-2, pp. 141-148 (1991).
Basher et al. "Antibody targeting tumor-derived soluble NKG2D ligand sMIC reprograms NK cell homeostatic survival and function and enhances melanoma response to PDL1 blockade therapy", Journal of Hematology & Oncology 13:74, pp. 1-16 (2020).
Basher et al., "Cooperative therapeutic anti-tumor effect of IL-15 agonist ALT-803 and co-targeting soluble NKG2D ligand sMIC", Oncotarget 7, pp. 814-830 (2016).
Da Silva et al., "MICA/B antibody induces macrophage-mediated immunity against acute myeloid leukemia", Blood 139 (2): pp. 205-216 (2022).
De Andrade et al., "Antibody-mediated inhibition of MICA and MICB shedding promotes NK cell-driven tumor immunity", Science 359(6383), pp. 1537-1542 (2018).
De Andrade et al., "Inhibition of MICA and MICB Shedding Elicits NK cell-mediated Immunity against Tumors Resistant to Cytotoxic T cells", Cancer Immunol Res. 8(6), pp. 769-780 (2020).
Dhar et al., "Tumor-derived NKG2D ligand sMIC reprograms NK cells to an inflammatory phenotype through CBM signalosome activation", Communications Biology 4:905, pp. 1-16 (2021).

(Continued)

*Primary Examiner* — Michael Allen

(74) *Attorney, Agent, or Firm* — McNeill PLLC

(57) ABSTRACT

The present invention provides MIC antibodies, antigen binding portions thereof and MIC binding agents thereof for use in the treatment of cancer.

19 Claims, 6 Drawing Sheets

Specification includes a Sequence Listing.

(56) References Cited

OTHER PUBLICATIONS

Du et al., "MICA immune complex formed with alpha 3 domain-specific antibody activates human NK cells in a Fc-dependent manner", Journal for Immunotherapy, 7:207, pp. 1-13, (2019).

Groh et al., "Tumour-derived soluble MIC ligands impair expression of NKG2D and T-cell activation", Nature 419, pp. 734-738 (2002).

Holdenrieder et al., "Soluble MICA in malignant diseases", Int. J. Cancer 118, pp. 684-687 (2006).

Holdenrieder et al., "Soluble MICB in malignant diseases: analysis of diagnostic significance and correlation with soluble MICA", Cancer Immunol Immunother 55, pp. 1584-1589 (2006).

Liu et al., "Perturbation of NK cell peripheral homeostasis accelerates prostate carcinoma metastasis," J Clin Invest., 123(10): pp. 4410-4422 (2013).

Lu et al., "Nonblocking Monoclonal Antibody Targeting Soluble MIC Revamps Endogenous Innate and Adaptive Antitumor Responses and Eliminates Primary and Metastatic Tumors", Clinical Cancer Research 21(21), pp. 4819-4830 (2015).

Luo et al., "Tumor-Derived Soluble MICA Obstructs the NKG2D Pathway to Restrain NK Cytotoxicity," Aging and Disease 11(1), pp. 118-128 (2020).

Mantovani et al., "An Anti-MICA/B Antibody and IL-15 Rescue Altered NKG2D-Dependent NK Cell Responses in Hepatocellular Carcinoma", Cancers 12: pp. 1-15 (2020).

Rebmann et al. "Soluble MICA as an independent prognostic factor for the overall survival and progression-free survival of multiple myeloma patients", Clinical Immunology 123: pp. 114-120 (2007).

Whalen et al., "CLN 619 A Clinical Stage MICA B Specific IgG1 Antibody Which Restores the MICA B-NKG2D Axis Requires Fc Function for Potent Anti-Tumor Activity", J. Immunotherapy Cancer, 10(Suppl 2):A1450 (2022).

Xiao et al., "Soluble NKG2D ligand promotes MDSC expansion and skews macrophage to the alternatively activated phenotype", J Hematol Oncol 8:13, pp. 1-10 (2015).

Zhang et al., "Antibody targeting tumor-derived soluble NKG2D ligand sMIC provides dual costimulation of CD8 T cells and enables sMIC+ tumors respond to PD1/PD-L1 blockade therapy", Journal for Immuno Therapy of Cancer 7:223, pp. 1-15 (2019).

Zhang et al., "Antibody-mediated neutralization of soluble MIC significantly enhances CTLA4 blockade therapy", Science Advances 3:e1602133, pp. 1-12 (2017).

Yalcin et al., "Anti-Tumor Efficacy and Therapeutic Index Associated with Inhibition of Proteolytic Cleavage of the NKG2D Ligands MICA and MICB", Poster # 5561 at American Association for Cancer Research Annual Meeting 2020.

\* cited by examiner

MIC ANTIBODIES AND BINDING AGENTS AND METHODS OF USING THE SAME

CROSS-REFERENCE TO RELATED APPLICATION

This application is a continuation of International Application No. PCT/US2021/040445, filed Jul. 6, 2021, which claims the benefit of priority of U.S. Provisional Application No. 63/049,012 filed Jul. 7, 2020, each of which is incorporated by reference herein in its entirety for any purpose.

STATEMENT REGARDING SPONSORED FUNDING

This invention was made with government support under Small Business Technology Transfer Grant 1R41CA206688-01A1 awarded by the US Small Business Administration. The government has certain rights in the invention.

SEQUENCE LISTING

This application contains a sequence listing, which has been submitted electronically in XML file format and is hereby incorporated by reference in its entirety. Said XML file, created on Oct. 4, 2023, is named "01301-0001-00US_ST26.xml" and is 50,860 bytes in size.

BACKGROUND

Major Histocompatibility Complex class I chain-related molecules A and B (MICA and MICB, respectively, generally termed MIC) are a family of proteins that bind to NKG2D. NKG2D is an activating immune receptor expressed by natural killer (NK) cells, NKT cells, subsets of gamma-delta T cells, and human CD 8 T cells. Binding of MIC to NKG2D on NK cells or T cells leads to, among other effects, activating NK cells and co-stimulating CD8 and gamma-delta T cells in vitro.

It has been reported that MIC family molecules are expressed on tumor cells and are believed to be involved in suppression of an immune response to the tumor cells. MICA is more frequently and abundantly expressed on tumor cells surface than MICB. MIC protein is found in both a membrane bound form and a soluble form, sMIC, the latter form shed from tumor cells. Elevation of serum levels of sMIC is associated with many types of cancer, including carcinomas, such as a solid tumor, e.g., melanoma, prostate cancer, ovarian cancer, cervical cancer, breast cancer, lung cancer, colon cancer, kidney cancer, gastrointestinal (GI) cancers, and head and neck cancer, and hematopoietic cancers, such as lymphomas and multiple myelomas, and bone and soft tissue originated cancers, such as sarcomas. A membrane restricted form of MIC(B) has been reported to sustain NKG2D-mediated protective anti-tumor immunity in mice, while the soluble form was correlated with tumor progression mediated by reducing NKG2D expression on NK cells and CD8 T cells and impairment of peripheral maintenance of NK cells. Agents that bind to sMIC therefore, represent a potential therapeutic approach for patients. There remains a need, however, for agents optimized for treatment of MIC+ cancers in humans.

SUMMARY OF THE INVENTION

The invention disclosed herein is based in part on MIC binding antibodies, antigen-binding portions thereof and related binding agents that specifically bind to soluble MIC (sMIC) and/or cell membrane-bound MIC (also referred to as membrane-bound MIC) and exhibit improved therapeutic properties. MIC, and sMIC in particular, is an important and advantageous therapeutic target for the treatment of certain cancers. These MIC-binding antibodies, antigen binding portions thereof and binding agents provide compositions and methods based on the use of such antibodies, antigen binding portions and related binding agents in the treatment of MIC+ cancers. Accordingly, the invention provides methods, compositions, kits, and articles of manufacture related to MIC binding agents.

In some embodiments, provided is a binding agent comprising (i) a heavy chain variable region having the amino acid sequence set forth in SEQ ID NO:1, and (ii) a light chain variable region having the amino acid sequence set forth in SEQ ID NO:2, wherein the heavy and light chain framework regions are optionally modified with from 1 to 8 amino acid substitutions, deletions or insertions in the framework regions. The binding agent specifically binds to MIC. In some embodiments, the binding agent specifically binds to MIC with a binding affinity greater than that of antibody B10G5. In some embodiments, the binding agent comprises (i) a heavy chain variable region having the amino acid sequence set forth in SEQ ID NO:1, and (ii) a light chain variable region having the amino acid sequence set forth in SEQ ID NO:2. The binding agent specifically binds to MIC. In some embodiments, the binding agent specifically binds to MIC with a binding affinity greater than that of antibody B10G5.

In some embodiments, provided is a binding agent comprising a heavy chain variable (VH) region and a light chain variable (VL) region, wherein the VH region comprises a complementarity determining region HCDR1 having the amino acid sequence set forth in SEQ ID NO:11, a HCDR2 having the amino acid sequence set forth in SEQ ID NO:12 and a HCDR3 having the amino acid sequence set forth in SEQ ID NO:13, and the VL region comprises a LCDR1 having the amino acid sequence set forth in SEQ ID NO:14, a LCDR2 having the amino acid sequence set forth in SEQ ID NO:15, and a LCDR3 having the amino acid sequence set forth in SEQ ID NO:16, and wherein the VH and VL region each comprise a humanized framework region. In some embodiments, the humanized VH framework region is derived from a human germline gene having the amino acid sequence set forth in IMGT IGHV4-59*11 (SEQ ID NO:29) and IGHJ4*01 (SEQ ID NO:30) or IGHV4-30-4*01 (SEQ ID NO:31) and IGHJ4*01 (SEQ ID NO:30). In some embodiments, the humanized VL framework region is derived from a human germline gene having the amino acid sequence set forth in IMGT IGKV1-NL1*01 (SEQ ID NO:32) and IMGT IGKJ1*01 (SEQ ID NO:33), IMGT IGKV1-33*01 (SEQ ID NO:34) and IMGT IGKJ1*01 (SEQ ID NO:33) or IMGT IGKV1-5*01 (SEQ ID NO:35) and IMGT IGKJ1*01 (SEQ ID NO:33). The binding agent specifically binds to MIC. In some embodiments, the binding agent specifically binds to MIC with a binding affinity greater than that of antibody B10G5.

In some embodiments, the binding agent is an antibody or an antigen-binding portion thereof. In some embodiments, the binding agent is a monoclonal antibody, a Fab, a Fab', a F(ab'), an Fv, a disulfide linked Fc, an scFv, a single domain antibody, a diabody, a bi-specific antibody, or a multi-specific antibody.

In some embodiments, the binding agent has a heavy chain variable region attached to a heavy chain constant region. In some embodiments, the heavy chain constant region is of the IgG isotype. In some embodiments, the heavy chain constant region is an IgG1 constant region. In some embodiments, the heavy chain constant region is an IgG4 constant region. In some embodiments, the heavy chain variable and constant regions have the amino acid sequence set forth in SEQ ID NO:3. In some embodiments, the binding agent has a light chain variable region attached to a light chain constant region. In some embodiments, the light chain constant region is of the kappa isotype. In some embodiments, the light chain variable and constant regions have the amino acid sequence set forth in SEQ ID NO:4. In some embodiments, the heavy chain constant region further comprises at least amino acid modification that increases binding affinity to human FcgammaRIII. In some embodiments, the heavy chain constant region further comprises at least amino acid modification that increases antibody dependent cytotoxicity (ADCC) activity. In some embodiments, the heavy chain constant region further comprises at least one amino acid modification that increases CDC activity.

In some embodiments, the binding agent is mono-specific. In some embodiments, the binding agent is mono-specific and bi-valent. In some embodiments, the binding agent is bi-valent. In some embodiments, the binding agent is bi-valent and bispecific or multi-valent and multi-specific.

In some embodiments, provided is a pharmaceutical composition comprising a binding agent of any of embodiments described herein and a pharmaceutically acceptable carrier.

In some embodiments, provided is a nucleic acid encoding a heavy chain variable region of a binding agent that has the amino acid sequence set forth in SEQ ID NO:1, optionally having the nucleic acid sequence set forth in SEQ ID NO:21. In some embodiments, provided is a nucleic acid encoding a light chain variable region of a binding agent that has the amino acid sequence set forth in SEQ ID NO:2, optionally having the nucleic acid sequence set forth in SEQ ID NO:22. In some embodiments provided is a nucleic acid encoding the binding agent of any of the embodiments described herein, optionally having the nucleic acid sequences set forth in SEQ ID NO:21 and SEQ ID NO:22. In some embodiments, provided is a vector comprising any of the nucleic acids encoding MIC binding agent polypeptides as described herein. In some embodiments, provided is a cell comprising a nucleic acid encoding any of the binding agent polypeptides described herein or a vector comprising such a nucleic acid(s).

In some embodiments, provided is a method of treating a MIC+ cancer, comprising administering to a subject in need thereof a therapeutically effective amount of a binding agent comprising (i) a heavy chain variable region having the amino acid sequence set forth in SEQ ID NO:1, and (ii) a light chain variable region having the amino acid sequence set forth in SEQ ID NO:2, wherein the heavy and light chain framework regions are optionally modified with from 1 to 8 amino acid substitutions, deletions or insertions in the framework regions, wherein the binding agent specifically binds to sMIC and/or membrane bound MIC. In some embodiments, the binding agent specifically binds to MIC with a binding affinity greater than that of antibody B10G5.

In some embodiments, provided is a method of treating a MIC+ cancer, comprising administering to a subject in need thereof a therapeutically effective amount of a binding agent comprises (i) a heavy chain variable region having the amino acid sequence set forth in SEQ ID NO:1, and (ii) a light chain variable region having the amino acid sequence set forth in SEQ ID NO:2, wherein the binding agent specifically binds to MIC. In some embodiments, the binding agent specifically binds to MIC with a binding affinity greater than that of antibody B10G5.

In some embodiments, provided is a method of treating a MIC+ cancer, comprising administering to a subject in need thereof a therapeutically effective amount of any of the binding agent embodiments described herein. In some embodiments, the methods include administering the binding agent as a pharmaceutical composition including a pharmaceutically acceptable carrier.

In some embodiments, the cancer is a carcinoma, a sarcoma, a neuroendocrine tumor, or a hematologic malignancy. In some embodiments, the carcinoma is a solid tumor, optionally selected from melanoma, prostate cancer, ovarian cancer, cervical cancer, breast cancer, lung cancer, colon cancer, kidney cancer, and head and neck cancer. In some embodiments, the hematologic malignancy is a lymphoma, leukemia, or multiple myeloma.

In some embodiments, the method further comprises administering an immunotherapy to the subject. In some embodiments, the immunotherapy is an adoptive cell therapy or a checkpoint inhibitor. In some embodiments, the adoptive cell therapy is selected from autologous NK cells, allogeneic NK cells, autologous T cells, CAR modified T cells and CAR modified NK cells. In some embodiments, the immunotherapy comprises a checkpoint inhibitor. In some embodiments, the checkpoint inhibitor is selected from an antibody that specifically binds to human PD-1, human PD-L1, or human CTLA4. In some embodiments, the checkpoint inhibitor is pembrolizumab, nivolumab, cemiplimab or ipilimumab.

In some embodiments, the methods include the step of not administering chemotherapy to the subject for at least four weeks, at least six weeks or at least eight weeks prior to the administration of the binding agent. In some embodiments, the binding agent is administered intravenously. In some embodiments, the binding agent is administered in a dose of about 0.1 mg/kg to about 100 mg/kg, or about 0.1 mg/kg to about 25 mg/kg, or about 0.1 mg/kg to about 20 mg/kg, or about 0.1 mg/kg to about 15 mg/kg, or about 0.1 mg/kg to about 10 mg/kg.

In some embodiments, provided is a method of reducing the level of circulating sMIC in a subject having cancer, comprising administering a therapeutically effective amount of a binding agent of any of the embodiments described herein or a pharmaceutical composition of any of the binding agent embodiments described herein, wherein the binding agent specifically binds to circulating sMIC. In some embodiments, the cancer is a carcinoma, a sarcoma, a neuroendocrine tumor, or a hematologic malignancy. In some embodiments, the carcinoma is selected from a solid tumor, including but not limited to, melanoma, prostate cancer, ovarian cancer, cervical cancer, breast cancer, lung cancer, colon cancer, kidney cancer, and head and neck cancer. In some embodiments, the hematologic malignancy is a lymphoma, leukemia or multiple myeloma.

In some embodiments, provided is a method of improving treatment outcome in a subject receiving immunotherapy, comprising administering an effective amount of an immunotherapy to the subject having cancer; and administering a therapeutically effective amount of a binding agent of any of the embodiments described herein or a pharmaceutical composition of any of the embodiments of a binding agent described herein, wherein the binding agent specifically binds to circulating sMIC and/or cell membrane-bound MIC; and wherein a treatment outcome of the subject is improved, as compared to administration of the immunotherapy alone. In some embodiments, the improved treatment outcome is an objective response selected from stable disease, a partial response or a complete response. In some embodiments, the improved treatment outcome is reduced tumor burden. In some embodiments, the improved treatment outcome is progression-free survival or disease-free survival. In some embodiments, the immunotherapy is an adoptive cell therapy or a checkpoint inhibitor. In some embodiments, the adoptive cell therapy is autologous NK cells, allogeneic NK cells, autologous T cells, CAR modified T cells and CAR modified NK cells. In some embodiments, the checkpoint inhibitor comprises an antibody that specifically binds to human PD-1, human PD-L1, or CTLA4. In some embodiments, the checkpoint inhibitor is pembrolizumab, nivolumab, cemiplimab or ipilimumab.

In some embodiments, chemotherapy is not administered to the subject for at least four weeks, at least six weeks or at least eight weeks prior to the administration of the binding agent. In some embodiments, the binding agent is administered intravenously. In some embodiments, the binding agent is administered in a dose of about 0.01 mg/kg to about 100 mg/kg, or about 0.01 mg/kg to about 25 mg/kg, or about 0.01 mg/kg to about 20 mg/kg, or about 0.01 mg/kg to about 15 mg/kg, about 0.01 mg/kg to about 10 mg/kg, about 0.1 mg/kg to about 100 mg/kg, or about 0.1 mg/kg to about 25 mg/kg, or about 0.1 mg/kg to about 20 mg/kg, or about 0.1 mg/kg to about 15 mg/kg, or about 0.1 mg/kg to about 10 mg/kg.

These and other aspects of the present invention may be more fully understood by reference to the following detailed description, non-limiting examples of specific embodiments and the appended drawings.

FIGURES

FIG. 2B), Kd=12.1 nM vs 7.2 nM, respectively, as determined by Bio-layer interferometry using an Octet Red96 (ForteBio).

Figure 4A:
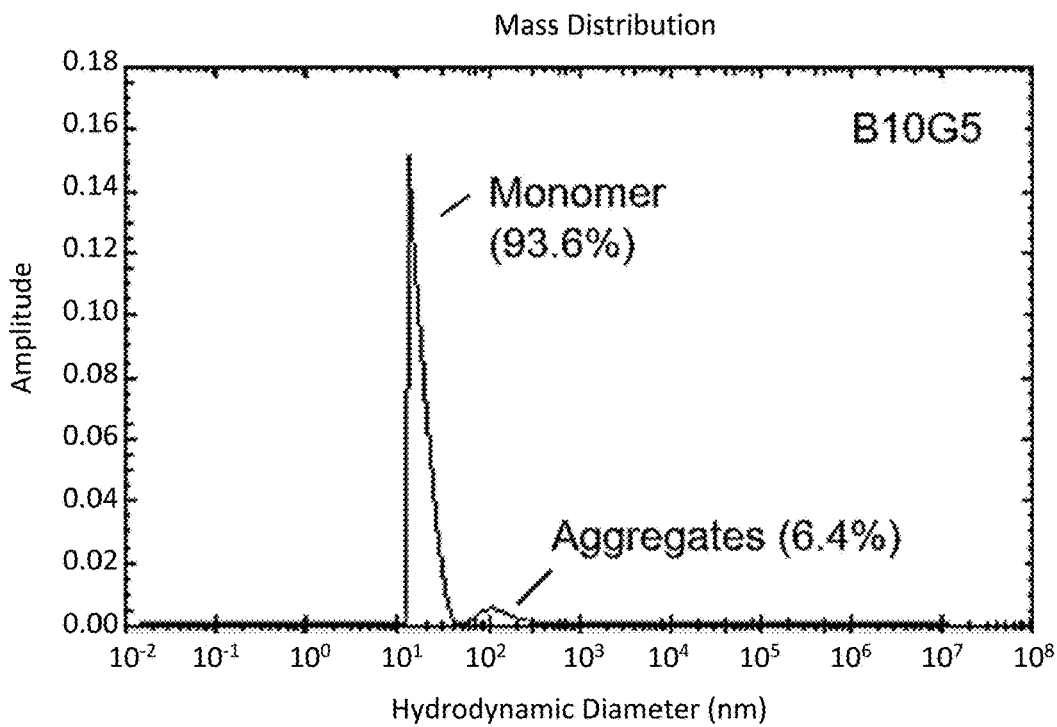
Figure 4B:
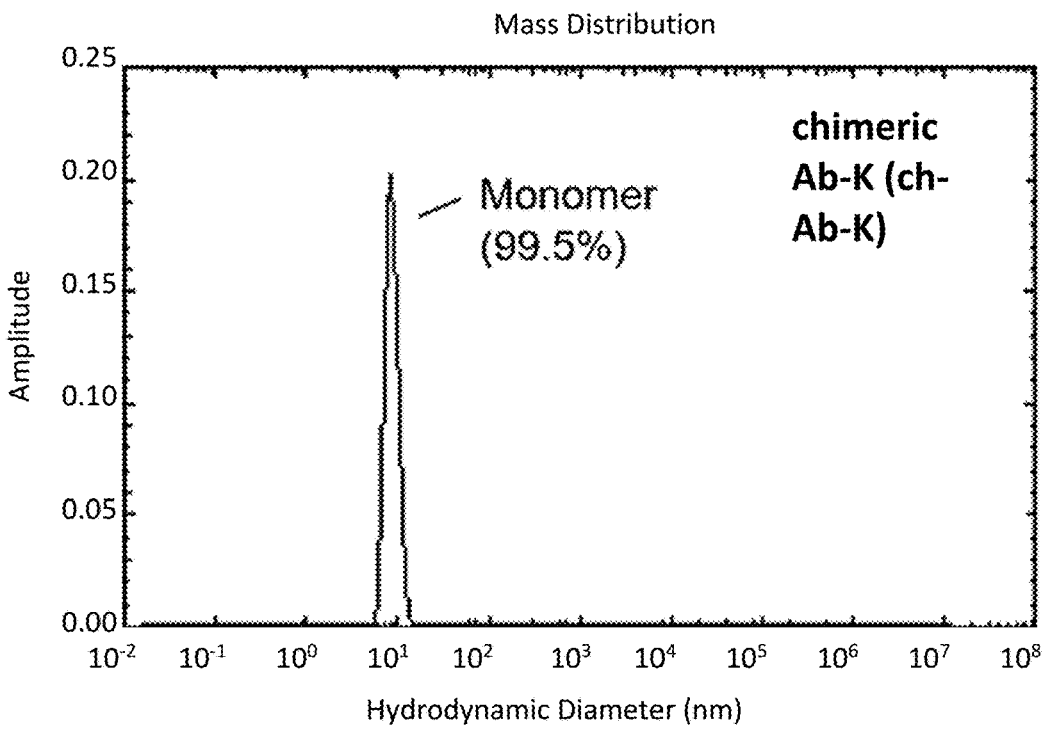
Figure 4C:
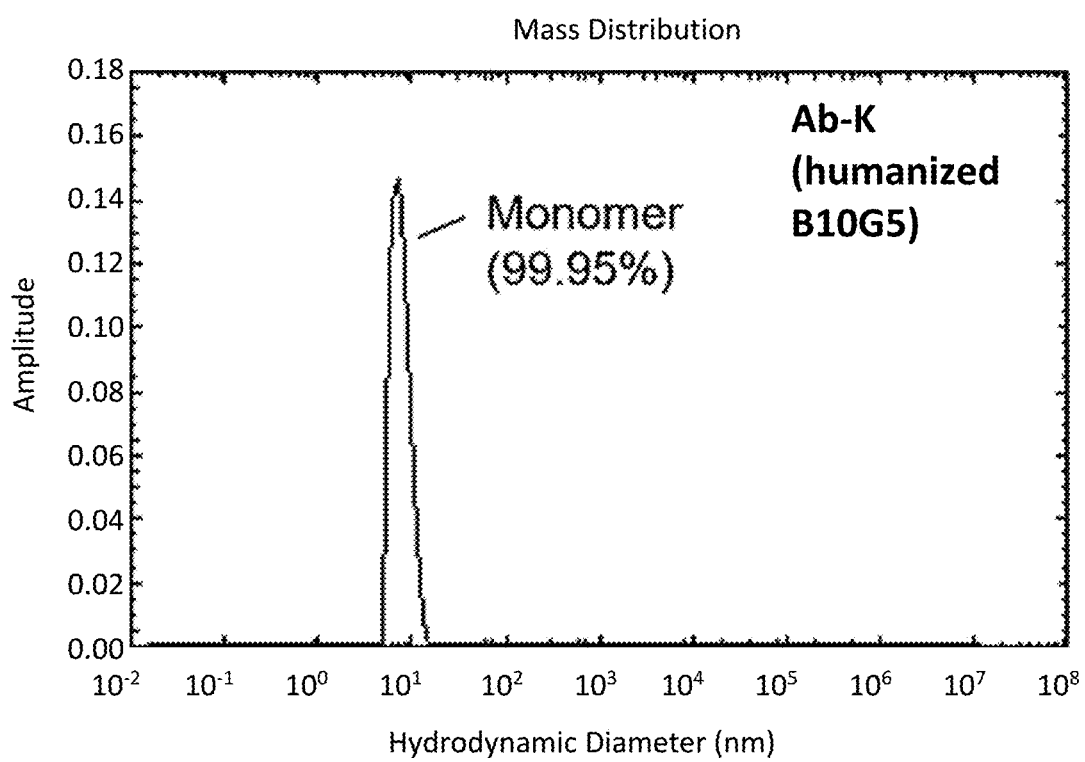

FIGS. 4A-4C show the levels of the antibody monomers and aggregates for murine antibody B10G5 (FIG. 4A), chimeric Ab-K antibody (ch-Ab-K, Ab-K variable domain and murine IgG1-Fc; FIG. 4B), and antibody K (Ab-K; humanized; FIG. 4C), as determined by Dynamic Light Scattering (DLS) assay.

DEFINITIONS

For convenience, certain terms in the specification, examples and claims are defined here. Unless stated otherwise, or implicit from context, the following terms and phrases have the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The terms "decrease," "reduce," "reduced", "reduction", "decrease," and "inhibit" are all used herein generally to mean a decrease by a statistically significant amount relative to a reference.

The terms "increased", "increase" or "enhance" or "activate" are all used herein to generally mean an increase by a statically significant amount relative to a reference.

The terms "isolated" or "partially purified" as used herein refer in the case of a nucleic acid, polypeptide or protein, to a nucleic acid, polypeptide or protein separated from at least one other component (e.g., nucleic acid or polypeptide or protein) that is present with the nucleic acid, polypeptide or protein as found in its natural source and/or that would be present with the nucleic acid, polypeptide or protein when expressed by a cell, or secreted in the case of secreted polypeptides and proteins. A chemically synthesized nucleic acid, polypeptide or protein, or one synthesized using in vitro transcription/translation, is considered "isolated." The terms "purified" or "substantially purified" refer to an isolated nucleic acid, polypeptide or protein that is at least 95% by weight the subject nucleic acid, polypeptide or protein, including, for example, at least 96%, at least 97%, at least 98%, at least 99% or more.

As used herein, the terms "protein" and "polypeptide" are used interchangeably herein to designate a series of amino acid residues each connected to each other by peptide bonds between the alpha-amino and carboxyl groups of adjacent residues. The terms "protein", and "polypeptide", also refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

Major Histocompatibility Complex class I chain-related (MIC) polypeptides are cell surface transmembrane proteins. MIC polypeptides include, but are not limited to human MICA isoforms (e.g. isoform 1, NCBI Ref Seq NP_000238.1 (SEQ ID NO:9) and 001170990) (these sequences are incorporated by reference herein) and other MICA isoforms), and human MICB isoforms (e.g. isoform 1, NCBI Ref Seq: NP_005922.2 (SEQ ID NO: 10) (the sequences are incorporated by reference herein) and other MICB isoforms). In some embodiments, a MIC polypeptide refers to MICA. In some embodiments, a MIC polypeptide refers to MICB. In some embodiments, a MIC polypeptide refers to the shared structural features of MICA and MICB, i.e., the epitope(s) shared by MICA and MICB.

As used herein, "soluble MIC" or "sMIC" refers to a portion of a MIC polypeptide (MICA or MICB) containing the alpha1 and alpha 2 domains and the alpha3 domain or a portion of the alpha 3 domain up to the proteolytic cleavage site and lacking the transmembrane domain (e.g., an extracellular portion of MIC). In some embodiments, soluble MICA can comprise the amino acid sequence set forth in Genbank Accession No. CAA77031.1 (SEQ ID NO:27), or a variant thereof, such as the amino acid sequences set forth in amino acid residues 24 to 297 of Genbank Accession No. AAU95072.1, AA045822.1, AFR69318.1, AFR69319.1 or AAH16929.1 or Ref Seq. NP_000238.1 or amino acids 1 to 274 of Genbank Accession No. CAE45581.1, or amino acids 1 to 273 of Genbank Accession No. AAD52069.1, AAD52070.1, or QDW65494.1 (the disclosures of which are incorporated by reference herein). In some embodiments, soluble MICB can comprise the amino acid sequence set forth in Genbank Accession No.: ARB08539.1 (SEQ ID NO:28), AAB71646.1, AAB71647.1 or AAB71644.1, or a variant thereof, such as the amino acid sequences set forth in amino acid residues 24 to 297 of Genbank Accession No. AB016470.1, ABB51802.1, AAB42011.1, AAB71643.1, or Q29980.1, or Ref SEQ No. NP_005922.2 or amino acid 1 to 273 of Genbank Accession No. AAC39848.1 AEK67483.1, AFR7773.1, AXY93666.1, CAB72098.1, or AAC39849.1 (the disclosures of which are incorporated by reference herein). Unless otherwise noted, use of the term "MIC" is intended to refer to both cell membrane-bound and soluble forms of MIC.

As used herein, antibody B10G5 refers to the MIC antibody of the same designation described in U.S. Pat. No. 9,803,017 (the disclosure of which is incorporated by reference herein for all purposes).

As used herein, an "epitope" refers to the amino acids conventionally bound by an immunoglobulin VH/VL pair, such as the antibodies and binding agents described herein. An epitope can be formed on a polypeptide from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An epitope defines the minimum binding site for an antibody or other binding agent, and thus represent the target of specificity of an antibody, antigen binding portion thereof or other immunoglobulin-based binding agent. In the case of a single domain antibody, an epitope represents the unit of structure bound by a variable domain in isolation.

As used herein, "specifically binds" refers to the ability of a binding agent (e.g., an antibody or portion thereof) described herein to bind to a target, such as MIC, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the binding agent and the concentration of target polypeptide. The person of ordinary skill in the art can determine appropriate conditions under which the antibodies and other binding agents described herein selectively bind to MIC using any suitable methods, such as titration of a binding agent in a suitable cell binding assay. A binding agent specifically bound to MIC is not displaced by a non-similar competitor. In certain embodiments, a MIC antibody or antigen-binding portion thereof is said to specifically bind to MIC when it preferentially recognizes its target antigen, MIC, in a complex mixture of proteins and/or macromolecules.

In some embodiments, a MIC antibody or antigen-binding portion thereof or other binding agent as described herein specifically binds to a MIC polypeptide with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, a MIC antibody or antigen-binding portion thereof or other binding agent as described herein specifically binds to a MIC polypeptide with a dissociation constant (KD) of from about $10^{-5}$ M to $10^{-6}$ M. In some embodiments, a MIC antibody or antigen-binding portion thereof or other binding agent as described herein specifically binds to a MIC polypeptide with a dissociation constant (KD) of from about $10^{-6}$ M to $10^{-7}$ M. In some embodiments, a MIC antibody or antigen-binding portion thereof or other binding agent as described herein specifically binds to a MIC polypeptide with a dissociation constant (KD) of from about $10^{-7}$ M to $10^{-8}$ M. In some embodiments, a MIC antibody or antigen-binding portion thereof or other binding agent as described herein specifically binds to a MIC polypeptide with a dissociation constant (KD) of from about $10^{-8}$ M to $10^{-9}$ M. In some embodiments, a MIC antibody or antigen-binding portion thereof or other binding agent as described herein specifically binds to a MIC polypeptide with a dissociation constant (KD) of from about $10^{-9}$ M to $10^{-10}$ M. In some embodiments, a MIC antibody or antigen-binding portion thereof or other binding agent as described herein specifically binds to a MIC polypeptide with a dissociation constant (KD) of from about $10^{-10}$ M to $10^{-11}$ M. In some embodiments, a MIC antibody or antigen-binding portion thereof or other binding agent as described herein specifically binds to a MIC polypeptide with a dissociation constant (KD) of from about $10^{-11}$ M to $10^{-12}$ M. In some embodiments, a MIC antibody or antigen-binding portion thereof or other binding agent as described herein specifically binds to a MIC polypeptide with a dissociation constant (KD) of less than $10^{-12}$ M.

As used herein, the phrase "specifically binds to MIC with a binding affinity greater than that of antibody B10G5" refers to the binding affinity to soluble MIC.

As used herein, the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

Other than in the examples, or where otherwise indicated, all numbers expressing quantities of ingredients or reaction conditions used herein should be understood as modified in all instances by the term "about." The term "about" when used in connection with percentages can mean+/−1%.

The term "statistically significant" or "significantly" refers to statistical significance and generally means a two standard deviation (2SD) difference, above or below a reference value.

Other terms are defined herein within the description of the various aspects of the invention.

DETAILED DESCRIPTION

Provided herein are MIC binding antibodies (also referred to as a MIC antibody or MIC binding antibody) and antigen binding portions thereof that specifically bind to MIC. The MIC antibodies surprisingly exhibit improved properties, as compared to antibody B10G5. In some embodiments, the MIC antibody reduces the level of free sMIC in circulation in a subject. In some embodiments, the MIC binding antibody or antigen binding portion thereof comprises (i) a heavy chain variable region having the amino acid sequence set forth in SEQ ID NO:1, and (ii) a light chain variable region having the amino acid sequence set forth in SEQ ID NO:2. In some embodiments, the MIC binding antibody or antigen binding portion thereof comprises (i) a heavy chain variable region having the amino acid sequence set forth in SEQ ID NO:1 and (ii) a light chain variable region having the amino acid sequence set forth in SEQ ID NO:2, wherein the heavy and light chain variable framework regions are optionally modified with from 1 to 8, 1 to 6, 1 to 4 or 1 to 2 conservative amino acid substitutions in the framework regions, wherein the CDRs of the heavy or light chain variable regions are not modified. In some embodiments, the MIC binding antibody or antigen binding portion thereof comprises (i) a heavy chain variable region having the amino acid sequence set forth in SEQ ID NO:1 and (ii) a light chain variable region having the amino acid sequence set forth in SEQ ID NO:2, wherein the heavy and light chain variable framework regions are optionally modified with from 1 to 8, 1 to 6, 1 to 4 or 1 to 2 amino acid substitutions, deletions or insertions in the framework regions, wherein the CDRs of the heavy or light chain variable regions are not modified. In further aspects of any of these embodiments, the MIC binding antibody or antigen binding portion thereof specifically binds to MIC with a binding affinity greater than that of antibody B10G5.

In some embodiments, provided herein is a binding agent comprising: (i) a heavy chain variable region having the amino acid sequence set forth in SEQ ID NO:1, and (ii) a light chain variable region having the amino acid sequence set forth in SEQ ID NO:2, wherein the binding agent specifically binds to MIC. In some embodiments, provided herein is a binding agent comprising (i) a heavy chain variable region having the amino acid sequence set forth in SEQ ID NO:1 and (ii) a light chain variable region having the amino acid sequence set forth in SEQ ID NO:2, wherein the heavy and light chain variable framework regions are optionally modified with from 1 to 8, 1 to 6, 1 to 4 or 1 to 2 conservative amino acid substitutions in the framework regions and wherein the CDRs of the heavy or light chain variable regions are not modified. In some embodiments, provided herein is a binding agent comprising (i) a heavy chain variable region having the amino acid sequence set forth in SEQ ID NO:1 and (ii) a light chain variable region having the amino acid sequence set forth in SEQ ID NO:2, wherein the heavy and light chain variable framework regions are optionally modified with from 1 to 8, 1 to 6, 1 to 4 or 1 to 2 amino acid substitutions, deletions or insertions in the framework regions and wherein the CDRs of the heavy or light chain variable regions are not modified. As described herein, a binding agent includes a MIC antibody or antigen binding portion(s) thereof and can include other peptides or polypeptides covalently attached to the MIC antibody or antigen binding portion thereof. In any of these embodiments, the binding agent specifically binds to MIC. In some embodiments, the binding agent specifically binds to MIC with a binding affinity greater than that of antibody B10G5.

In some embodiments, provided is a binding agent comprising a heavy chain variable (VH) region and a light chain variable (VL) region, wherein the VH region comprises a complementarity determining region HCDR1 having the amino acid sequence set forth in SEQ ID NO:11, a HCDR2 having the amino acid sequence set forth in SEQ ID NO:12 and a HCDR3 having the amino acid sequence set forth in SEQ ID NO:13, and the VL region comprises a LCDR1 having the amino acid sequence set forth in SEQ ID NO:14, a LCDR2 having the amino acid sequence set forth in SEQ ID NO:15, and a LCDR3 having the amino acid sequence set forth in SEQ ID NO:16, and wherein each VH and VL comprises a humanized framework region. In some embodiments, the VH framework region is derived from a human germline gene having the amino acid sequence set forth in IMGT IGHV4-59*11 (SEQ ID NO:29) and IGHJ4*01 (SEQ ID NO:30) or IGHV4-30-4*01 (SEQ ID NO:31) and IGHJ4*01 (SEQ ID NO:30). In some embodiments, the VL framework region is derived from a human germline gene having the amino acid sequence set forth in IMGT IGKV1-NL1*01 (SEQ ID NO:32) and IMGT IGKJ1*01 (SEQ ID NO:33), IMGT IGKV1-33*01 (SEQ ID NO:34) and IMGT IGKJ1*01 (SEQ ID NO:33) or IMGT IGKV1-5*01 (SEQ ID NO:35) and IMGT IGKJ1*01 (SEQ ID NO:33).

In some embodiments, provided is a binding agent comprising a heavy chain variable (VH) region and a light chain variable (VL) region, wherein the VH region comprises a complementarity determining region HCDR1 having the amino acid sequence set forth in SEQ ID NO:11, a HCDR2 having the amino acid sequence set forth in SEQ ID NO:12 and a HCDR3 having the amino acid sequence set forth in SEQ ID NO:13, and wherein the VH region comprises an amino acid sequence that is at least 85%, at least 90%, at least 91%, at least 92%, at least 93%, at least 94%, at least 95%, at least 96%, at least 97%, at least 98%, or at least 99% identical to the amino acid sequence of SEQ ID NO: 1.

In some embodiments, provided is a binding agent comprising a heavy chain variable (VH) region and a light chain variable (VL) region, wherein the VL region comprises a LCDR1 having the amino acid sequence set forth in SEQ ID NO:14, a LCDR2 having the amino acid sequence set forth in SEQ ID NO:15, and a LCDR3 having the amino acid sequence set forth in SEQ ID NO:16, and wherein the VL region comprises an amino acid sequence that is at least 85%, at least 90%, at least 91%, at least 92%, at least 93%, at least 94%, at least 95%, at least 96%, at least 97%, at least 98%, or at least 99% identical to the amino acid sequence of SEQ ID NO: 2.

In some embodiments, provided is a binding agent comprising a heavy chain variable (VH) region and a light chain variable (VL) region, wherein the VH region comprises a complementarity determining region HCDR1 having the amino acid sequence set forth in SEQ ID NO:11, a HCDR2 having the amino acid sequence set forth in SEQ ID NO:12 and a HCDR3 having the amino acid sequence set forth in SEQ ID NO:13, and wherein the VH region comprises an amino acid sequence that is at least 85%, at least 90%, at least 91%, at least 92%, at least 93%, at least 94%, at least 95%, at least 96%, at least 97%, at least 98%, or at least 99% identical to the amino acid sequence of SEQ ID NO: 1; and wherein the VL region comprises a LCDR1 having the amino acid sequence set forth in SEQ ID NO:14, a LCDR2 having the amino acid sequence set forth in SEQ ID NO:15, and a LCDR3 having the amino acid sequence set forth in SEQ ID NO:16, and wherein the VL region comprises an amino acid sequence that is at least 85%, at least 90%, at least 91%, at least 92%, at least 93%, at least 94%, at least 95%, at least 96%, at least 97%, at least 98%, or at least 99% identical to the amino acid sequence of SEQ ID NO: 2.

In some embodiments, provided is a binding agent comprising a heavy chain that comprises a heavy chain variable (VH) region and a light chain that comprises a light chain variable (VL) region, wherein the VH region comprises a complementarity determining region HCDR1 having the amino acid sequence set forth in SEQ ID NO:11, a HCDR2 having the amino acid sequence set forth in SEQ ID NO:12 and a HCDR3 having the amino acid sequence set forth in SEQ ID NO:13, and wherein the VH region comprises the amino acid sequence of SEQ ID NO: 1; and wherein the VL region comprises a LCDR1 having the amino acid sequence set forth in SEQ ID NO:14, a LCDR2 having the amino acid sequence set forth in SEQ ID NO:15, and a LCDR3 having the amino acid sequence set forth in SEQ ID NO:16, and wherein the VL region comprises the amino acid sequence of SEQ ID NO: 2; and wherein the heavy chain comprises an amino acid sequence that is at least 85%, at least 90%, at least 91%, at least 92%, at least 93%, at least 94%, at least 95%, at least 96%, at least 97%, at least 98%, or at least 99% identical to the amino acid sequence of SEQ ID NO: 3, and wherein the light chain comprises an amino acid sequence that is at least 85%, at least 90%, at least 91%, at least 92%, at least 93%, at least 94%, at least 95%, at least 96%, at least 97%, at least 98%, or at least 99% identical to the amino acid sequence of SEQ ID NO: 4. In some embodiments, provided herein is a binding agent comprising a heavy chain comprising the amino acid sequence of SEQ ID NO: 3 and a light chain comprising the amino acid sequence of SEQ ID NO: 4. In some such embodiments, the binding agent is an antibody.

In some embodiments, a binding agent provided herein, such as an MIC antibody, exhibits good thermostability and/or low level of aggregates (such as high molecular weight (HMW) aggregates). The thermostability of the MIC antibody may be assessed, for example, by Tm and Tagg, which can be respectively obtained by intrinsic protein fluorescence (IPF) (266 nm excitation, 280-450 nm emission scan) and by static light scattering (SLS) at 473 nm using the Uncle system (Unchained Labs). The level of aggregates of MIC antibodies may be measured, for example, by using HPLC-SEC or by using dynamic light scattering (DLS). In some embodiments, the level of HMW aggregates of MIC antibodies—as a percentage of the total amount of MIC antibodies—may be less than 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1%, or 0.5%, based on the peak areas of monomer and HMW aggregates of antibodies. In other words, at least 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, or 99.5% of the MIC antibodies exist in monomer form when in solution. In some embodiments, the polydispersity index (PDI) of MIC antibodies may be less than 0.1, as determined by DLS.

In specific embodiments, a MIC antibody or antigen binding portion thereof or other binding agent specifically binds to a conformational epitope on MICA and MICB located within about amino acid positions 66-77, 136-144 and 247-258 of the amino acid sequence set forth in SEQ ID NO:27 or 28. In specific embodiments, a MIC antibody or antigen binding portion or other binding agent has (i) a heavy chain variable region having the amino acid sequence set forth in SEQ ID NO:1, and (ii) a light chain variable region having the amino acid sequence set forth in SEQ ID NO:2, and has an optionally substituted framework region as described herein, and competes for specific binding with the antibody B10G5 that specifically binds to a conformational epitope on MICA and MICB location within about amino acid 66-77, 136-144 and 247-258 of the amino acid sequence set forth in SEQ ID NO:27 and 28.

In some embodiments, the compositions and methods described herein relate to inhibition of the immune suppressive effects of sMIC (e.g., reducing the level and/or activity of sMIC that is available to interact with cellular receptor NKG2D) by a MIC antibody, antigen binding portion thereof or other binding agent in vivo. In some embodiments, inhibition of sMIC can be a reduction of serum levels of unbound MIC and restoration of cell surface NKG2D expression on NK and CD8 T cells. In some embodiments, inhibition of sMIC can be a reduction of the level of MIC (e.g. the level of sMIC in circulation).

As used herein, the term "antibody" refers to immunoglobulin molecules and immunologically active portions of immunoglobulin molecules, i.e., molecules that contain an antigen binding site that specifically binds to an antigen. The term generally refers to antibodies comprised of two immunoglobulin heavy chain variable regions and two immunoglobulin light chain variable regions including full length antibodies (having heavy and light chain constant regions) and antigen-binding portions thereof; including, for example, an intact monoclonal antibody, a Fab, a Fab', a F(ab')$_2$, a Fv, a disulfide linked Fv, a scFv, a single domain antibody (dAb), a diabody, a multi-specific antibody, a dual specific antibody, a bispecific antibody, and single chains (see, e.g., Huston et al., Proc. Natl. Acad. Sci. U.S.A., 85, 5879-5883 (1988) and Bird et al., Science 242, 423-426 (1988), which are incorporated herein by reference).

Each heavy chain is composed of a variable region (abbreviated as VH) and a constant region. The heavy chain constant region may include three domains CH1, CH2 and CH3 and optionally a fourth domain, CH4. Each light chain is composed of a variable region (abbreviated as VL) and a constant region. The light chain constant region is a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs that are arranged from the N terminus to the C terminus in the following order: FR1, CDR1, FR2, CDR2, FR3, CDR3, and FR4. This structure is well known to those skilled in the art.

The amino acid sequences of the VH CDRs of the MIC antibody are set forth in SEQ ID NO:1 at amino acids 26 34 (GYSITSDYA, HCDR1, SEQ ID NO:11), 50-58 (GYISYS-GST, HCDR2, SEQ ID NO:12) and 97-105 (ARGGTYFDY, HCDR3, SEQ ID NO:13). The amino acid sequences of the VL CDRs of the MIC antibody are set forth in SEQ ID NO:2 at amino acids 24-32 (RASAHINNW, LCDR1, SEQ ID NO:14), 50-56 (DATSLES, LCDR2, SEQ ID NO:15) and 98-107 (QHYWSTPWT, LCDR3, SEQ ID NO:16). The phrase "wherein the CDRs of the heavy or light chain variable regions are not modified" refers to these VH and VL CDRs (SEQ ID NOs:11-16), which do not have amino acid substitutions, deletions or insertions.

As used herein, an "antigen-binding portion" of a MIC antibody refers to the portions of a MIC antibody as described herein having the VH and VL sequences of the MIC antibody (set forth in SEQ ID NO:1 and SEQ ID NO:2, optionally modified as described herein). In accordance with the term "antigen-binding portion" of an antibody, examples of antigen binding portions include a Fab, a Fab', a F(ab')$_2$, a Fv, a disulfide linked Fv, a scFv, a single domain antibody (dAb), a diabody, and single chains. As used herein, the terms Fab, F(ab')$_2$ and Fv refer to the following: (i) an Fab fragment, i.e. a monovalent fragment composed of the VL, VH, CL and CH1 domains; (ii) an F(ab')₂ fragment, i.e. a bivalent fragment comprising two Fab fragments linked to one another in the hinge region via a disulfide bridge; and (iii) an Fv fragment composed of the VL and VH domains of a MIC antibody. Although the two domains of the Fv fragment, namely VL and VH, are encoded by separate coding regions, they may further be linked to one another using a synthetic linker, e.g. a poly-G4S amino acid sequence ('(G4S)n' disclosed as SEQ ID NO: 17, wherein n=1 to 5), making it possible to prepare them as a single protein chain in which the VL and VH regions combine in order to form monovalent molecules (known as single chain Fv (ScFv)). The term "antigen-binding portion" of an antibody is also intended to include such single chain antibodies. Other forms of single chain antibodies such as "diabodies" are likewise included here. Diabodies are bivalent, bispecific antibodies in which VH and VL domains are expressed on a single polypeptide chain, but using a linker connecting the VH and VL domains is too short for the two domains to be able to combine on the same chain, thereby forcing the VH and VL domains to pair with complementary domains of a different chain (VL and VH, respectively), and to form two antigen-binding sites (see, for example, Holliger, R, et al. (1993) Proc. Natl. Acad. Sci. USA 90:64446448; Poljak, R. J, et al. (1994) Structure 2:1121-1123).

An immunoglobulin constant region refers to a heavy or light chain constant region. Human heavy chain and light chain constant region amino acid sequences are known in the art. A constant region can be of any suitable type, which can be selected from the classes of immunoglobulins, IgA, IgD, IgE, IgG, and IgM. Several immunoglobulin classes can be further divided into isotypes, e.g., IgG1, IgG2, IgG3, IgG4, or IgA1, and IgA2. The heavy-chain constant regions (Fc) that corresponds to the different classes of immunoglobulins can be α, δ, ε, γ, and μ, respectively. The light chains can be one of either kappa or K and lambda or A.

In some embodiments, a constant region can have an IgG1 isotype. In some embodiments, a constant region can have an IgG2 isotype. In some embodiments, a constant region can have an IgG3 isotype. In some embodiments, a constant region can have an IgG4 isotype. In some embodiments, an Fc domain can have a hybrid isotype comprising constant regions from two or more isotypes. In some embodiments, an immunoglobulin constant region can be an IgG1 or IgG4 constant region.

In some embodiments, a MIC antibody heavy chain is of the IgG1 isotype and has the amino acid sequence set forth in SEQ ID NO:7. In some embodiments, a MIC antibody light chain is of the kappa isotype and has the amino acid sequence set forth in SEQ ID NO:8.

Furthermore, a MIC antibody or an antigen-binding portion thereof may be part of a larger binding agent formed by covalent or noncovalent association of the antibody or antibody portion with one or more other proteins or peptides. Relevant to such binding agents are the use of the streptavidin core region in order to prepare a tetrameric scFv molecule (Kipriyanov, S. M., et al. (1995) Human Antibodies and Hybridomas 6:93-101) and the use of a cysteine residue, a marker peptide and a C-terminal polyhistidinyl peptide, e.g. hexahistidinyl tag (' hexahistidinyl tag' disclosed as SEQ ID NO: 18) in order to produce bivalent and biotinylated scFv molecules (Kipriyanov, S. M., et al. (1994) Mol. Immunol. 31:10471058).

As to the VH and VL amino acid sequences, one of skill will recognize that individual substitutions, deletions or additions (insertions) to a nucleic acid encoding the VH or VL, or amino acids in polypeptide that alter a single amino acid or a small percentage of amino acids in the encoded sequence is a "conservatively modified variant", where the alteration results in the substitution of an amino acid with a chemically similar amino acid (a conservative amino acid substitution) and the altered polypeptide retains the ability to specifically bind to MIC with a binding affinity greater than that of antibody B10G5.

In some embodiments, a conservatively modified variant of a MIC antibody or antigen binding portion thereof can have alterations in the FR (i.e., other than in the CDRs), e.g. a conservatively modified variant of a MIC antibody has the amino acid sequences of the VH and VL CDRs (set forth in SEQ ID NOs: 11-16) and has at least one conservative amino acid substitution in the FR. In some embodiments, the VH and VL amino acid sequences (set forth in SEQ ID NOs: 1 and 2, respectively) collectively have no more than 8 or 6 or 4 or 2 or 1 conservative amino acid substitutions in the FR, as compared to the amino acid sequences of the VH and VL (SEQ ID Nos: 1 and 2, respectively). In some embodiments, the VH and VL amino acid sequences (set forth in SEQ ID NOs: 1 and 2, respectively) have 8 to 1, 6 to 1, 4 to 1 or 2 to 1 conservative amino acid substitutions in the FR, as compared to the amino acid sequences of the VH and VL (set forth in SEQ ID Nos: 1 and 2, respectively). In further aspects of any of these embodiments, a conservatively modified variant of the MIC antibody, antigen binding portion thereof or other binding agent exhibits a binding affinity for MIC greater than the binding affinity of antibody B10G5.

For conservative amino acid substitutions, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative amino acid substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained, i.e., to MIC (sMIC and/or membrane bound MIC).

For conservative substitutions, amino acids can be grouped according to similarities in the properties of their side chains (in A. L. Lehninger, in Biochemistry, second ed., pp. 73-75, Worth Publishers, New York (1975)): (1) nonpolar: Ala (A), Val (V), Leu (L), Ile (I), Pro (P), Phe (F), Trp (N), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His (H).

Alternatively, for conservative substitutions naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. Non-conservative substitutions will entail exchanging a member of one of these classes or another class.

Particular conservative substitutions include, for example; Ala to Gly or to Ser; Arg to Lys; Asn to Gln or to His; Asp to Glu; Cys to Ser; Gln to Asn; Glu to Asp; Gly to Ala or to Pro; His to Asn or to Gln; Ile to Leu or to Val; Leu to Ile or to Val; Lys to Arg, to Gln or to Glu; Met to Leu, to Tyr or to Ile; Phe to Met, to Leu or to Tyr; Ser to Thr; Thr to Ser; Trp to Tyr; Tyr to Trp; and/or Phe to Val, to Ile or to Leu.

In some embodiments, a conservatively modified variant on a MIC antibody or antigen binding portion thereof preferably is at least 90%, at least 91%, at least 92%, at least 93%, at least 94%, at least 95%, at least 96%, at least 97%, at least 98%, at least 99%, or more, identical to the reference VH or VL sequence, wherein the VH and VL CDRs (SEQ ID NOs:11-16) are not modified. The degree of homology (percent identity) between the reference and modified sequence can be determined, for example, by comparing the two sequences using freely available computer programs commonly employed for this purpose on the world wide web (e.g. BLASTp or BLASTn with default settings).

In some embodiments, the VH and VL amino acid sequences (set forth in SEQ ID NOs:1 and 2, respectively) collectively have no more than 8 or 6 or 4 or 2 or 1 conservative amino acid substitutions in the framework regions, as compared to the amino acid sequences of the VH and VL (set forth in SEQ ID NOs: 1 and 2, respectively). In some embodiments, the VH and VL amino acid sequences (set forth in SEQ ID Nos: 1 and 2, respectively) collectively have 8 to 1, or 6 to 1, or 4 to 1, or 2 to 1 conservative amino acid substitutions in the framework regions, as compared to the amino acid sequences of the VH and VL (set forth in SEQ ID NOs: 1 and 2, respectively). In some embodiments, the VH and VL amino acid sequences (set forth in SEQ ID NOs: 1 and 2, respectively) collectively have no more than 8 or 6 or 4 or 2 or 1 amino acid substitutions, deletions or insertions in the framework regions, as compared to the amino acid sequences of the VH and VL (set forth in SEQ ID NOs: 1 and 2, respectively). In some embodiments, the VH and VL amino acid sequences (set forth in SEQ ID NOs: 1 and 2, respectively) have 8 to 1, 6 to 1, 4 to 1, or 2 to 1 conservative amino acid substitutions in the framework regions, as compared to the amino acid sequences of the VH and VL (set forth in SEQ ID NOs: 1 and 2, respectively). In some embodiments, the VH and VL amino acid sequences (set forth in SEQ ID NOs:1 and 2, respectively) collectively have no more than 8 or 6 or 4 or 2 or 1 amino acid substitutions, deletions or insertions, as compared to the amino acid sequences of the VH and VL (set forth in SEQ ID NOs:1 and 2, respectively).

Modification of a native (or reference) amino acid sequence can be accomplished by any of a number of techniques known to one of skill in the art. Mutations can be introduced, for example, at particular loci by synthesizing oligonucleotides containing the desired mutant sequence, flanked by restriction sites enabling ligation to fragments of the native sequence. Following ligation, the resulting reconstructed sequence encodes a variant having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion desired. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

In some embodiments, a MIC antibody or antigen-binding portion thereof has fully human constant regions. In some embodiments, a MIC antibody or antigen-binding portion thereof has non-human constant regions. In some embodiments, a MIC antibody heavy chain is of the IgG1 isotype and has the amino acid sequence set forth in SEQ ID NO:7. In some embodiments, a MIC antibody light chain is of the kappa isotype and has the amino acid sequence set forth in SEQ ID NO:8.

In some embodiments, a MIC antibody or antigen binding portion thereof has a modified constant region (Fc region) or Fc domain. Fc domains (e.g., CH1, CH2, CH3 and optionally CH4) are portions of an Fc region. Portions of an Fc domain or region can bind to Fc receptors (FcRs) on cells. FcRs are organized into classes (e.g., gamma (γ), alpha (α) and epsilon (ε)) based on the class of antibody that the FcR recognizes. The FcaR class can bind to IgA and includes several isoforms, such as FcaRI (CD89). The FcγR class can bind to IgG and includes several isoforms, FcγRI (CD64), FcγRIIA (CD32a), FcγRIIB (CD32b), FcγRIIIA (CD16a), and FcγRIIIB (CD16b). FcγRIIIA (CD16a) has two major variants, F158 or V158.

The binding of an Fc domain or Fc region to an FcR can modify an immune response, as compared to a reference. Similarly, the absence of binding of an Fc domain to an FcR can modify an immune response, as compared to a reference.

A MIC antibody can have an Fc domain having a sequence that has been modified, as compared to a wild type or reference sequence, to alter at least one constant domain or region-mediated biological effector function relative to the corresponding wild type or reference sequence. For example, in some embodiments, an Fc domain can be modified to reduce or to increase at least one constant domain or region-mediated biological effector function relative to an unmodified Fc domain, e.g., reduced or increased binding to an Fc receptor (FcR). FcR binding can be reduced or increased by, for example, modifying the immunoglobulin constant region segment of the antibody at a particular site(s) involved in (e.g., necessary for or affecting) FcR interactions. In some embodiments, the Fc domain is modified to reduce binding to one or more Fc gamma receptors (e.g., one or more of FcγRI, FcγRIIA, FcγRIIB, FcγRIIIA, FcγRIIIB, and/or FcRN).

In some embodiments, an antibody constant region or domain is modified to acquire or improve at least one constant region-mediated biological effector function relative to an unmodified Fc domain, e.g., to enhance FcγR interactions. For example, an antibody constant region or domain can be modified to bind to FcγRIIA, FcγRIIB and/or FcγRIIIA with greater affinity than the corresponding wild type Fc domain or region.

A modification in the amino acid sequence Fc domain can alter the recognition of an FcR for the Fc domain or region. However, such modifications can still allow for FcR-mediated signaling. A modification(s) can be a substitution of an amino acid at a residue for a different amino acid at that residue. A modification(s) can permit binding of an FcR to a site on the Fc domain or region that the FcR may not otherwise bind to. A modification(s) can increase binding affinity of an FcR to an Fc domain or region relative to the binding of a reference sequence. A modification(s) can decrease binding affinity of an FcR to a site on the Fc domain relative to the binding of a reference sequence.

In some embodiments, a modification(s) in the amino acid sequence Fc domain can alter the recognition of an FcR, or multiple FcRs, for the Fc domain or region. Such a modification(s) can alter the ability of the antibody or antigen binding portion to interact with immune cells. Such a modification or series of modifications to an Fc domain or region can permit selective binding of an Fc domain to FcRs on immune cells, or can reduce or eliminate the interaction of an antibody or antigen binding portion having the modified domain with immune cells. For example, modifications to an Fc domain can reduce binding of an Fc domain to Fc gamma receptors, but retain the ability of the Fc domain to bind to FcRn.

A modified Fc region or domain can have at least one amino acid change as compared to the sequence of the wild-type Fc region or domain. An amino acid change in an Fc region can allow the antibody or antigen binding portion thereof to bind to at least one Fc receptor with greater affinity compared to a wild-type or reference Fc region. An amino acid change in an Fc domain can allow the antibody to bind to at least one Fc receptor with greater affinity as compared to a wild-type or reference Fc domain. An amino acid change in an Fc region can allow the antibody to bind to at least one Fc receptor with decreased affinity as compared to a wild-type or reference Fc region. An amino acid change in an Fc domain can allow the antibody to bind to at least one Fc receptor with decreased affinity as compared to a wild-type or reference Fc domain.

In some embodiments, a MIC antibody or antigen binding portion thereof can have an Fc domain or Fc region comprising a sequence of the IgG1 isoform that has been modified from the wild type IgG1 sequence. A modification can comprise a substitution at one or more one amino acid residues of an Fc domain such as at 5 different amino acid residues including L235V/F243L/R292P/Y300L/P396L (IgGIVLPLL), according to the EU index of Kabat. A modification can comprise a substitution at one or more amino acid residues such as at 2 different amino acid residues of an Fc domain including S239D/I332E (IgG1DE), according to the EU index of Kabat. A modification can comprise a substitution at one or more amino acid residues such as at 3 different amino acid residues of an Fc domain including S298A/E333A/K334A (IgG1 AAA), according to the EU index of Kabat.

In some embodiments, an Fc domain or region of a MIC antibody or antigen binding portion thereof can exhibit reduced binding affinity to one or more Fc receptors. In some embodiments, an Fc domain or region can exhibit reduced binding affinity to one or more Fcgamma receptors. In some embodiments, an Fc domain or region can exhibit reduced binding affinity to FcRn receptors. In some embodiments, an Fc domain or region can exhibit reduced binding affinity to Fcgamma and to FcRn receptors. In some embodiments, an Fc domain is an Fc null domain or region. As used herein, an "Fc null" refers to a domain that exhibits weak to no binding to any of the Fcgamma receptors. In some embodiments, an Fc null domain or region exhibits a reduction in binding affinity (e.g., increase in Kd) to Fc gamma receptors of at least 1000-fold.

In some embodiments, the Fc domain or region of the MIC antibody is an Fc null domain or region comprising a flexible sequence, such as GGGS (SEQ ID NO: 38). In some embodiments, the MIC antibody is of the IgG1 isoform, and the flexible sequence is inserted between G237 and G238 of the human IgG1 heavy chain. In some embodiments, inclusion of the flexible sequence in the MIC antibody results in little to no effect on the binding affinity of the antibody. In some embodiments, inclusion of the flexible sequence in the MIC antibody reduces the ADCC activity of the antibody. In some embodiments, inclusion of the flexible sequence in the MIC antibody results in little to no loss of glycosylation and/or significant change(s) to the glycan profile of the antibody. Glycosylation and/or the glycan profile of the antibody may be measured, for example, by subjecting the antibody to PNGase F digestion, and analyzing the enzymatic products using hydrophilic interaction chromatography (HILIC) with a fluorescence detector.

In certain embodiments, an Fc domain has decreased binding affinity for one or more of FcγRI (CD64), FcγRIIA (CD32), FcγRIIIA (CD 16a), FcγRIIIB (CD 16b), or any combination thereof. In order to decrease binding affinity of an Fc domain or region to an Fc receptor, the Fc domain or region may comprise one or more amino acid substitutions that reduce the binding affinity of the Fc domain or region to an Fc receptor.

In some embodiments, the one or more substitutions comprise any one or more of IgG1 heavy chain substitutions corresponding to E233P, L234V, L234A, L235A, L235E, AG236, G237A, E318A, K320A, K322A, A327G, A330S, and/or P331S, according to the EU index of Kabat numbering. In some embodiments, a modification can be substitution of E233, L234 and L235, such as E233P/L234V/L235A or E233P/L234V/L235A/AG236, according to the EU index of Kabat. In some embodiments, a modification can be a substitution of P238, such as P238A, according to the EU index of Kabat. In some embodiments, a modification can be a substitution of D265, such as D265A, according to the EU index of Kabat. In some embodiments, a modification can be a substitution of N297, such as N297A, according to the EU index of Kabat. In some embodiments, a modification can be a substitution of A327, such as A327Q, according to the EU index of Kabat. In some embodiments, a modification can be a substitution of P329, such as P239A, according to the EU index of Kabat.

In some embodiments, an IgG Fc domain or region comprises at least one amino acid substitution that reduces its binding affinity to FcγRI, as compared to a wild-type or reference IgG Fc domain. In some embodiments, a modification can comprise a substitution at F241, such as F241A, according to the EU index of Kabat. In some embodiments, a modification can comprise a substitution at F243, such as F243A, according to the EU index of Kabat. In some embodiments, a modification can comprise a substitution at V264, such as V264A, according to the EU index of Kabat. In some embodiments, a modification can comprise a substitution at D265, such as D265A according to the EU index of Kabat.

In some embodiments, an IgG Fc domain or region comprises at least one amino acid substitution that increases its binding affinity to FcγRI, as compared to a wild-type or reference IgG Fc domain. In some embodiments, a modification can comprise a substitution at A327 and P329, such as A327Q/P329A, according to the EU index of Kabat.

In some embodiments, an IgG Fc modification(s) comprises substitution of one or more amino acids that reduce binding affinity of an IgG Fc domain or region to FcγRII and FcγRIIIA receptors. In some embodiments, a modification can be a substitution of D270, such as D270A, according to the EU index of Kabat. In some embodiments, a modification can be a substitution of Q295, such as Q295A, according to the EU index of Kabat. In some embodiments, a modification can be a substitution of A327, such as A237S, according to the EU index of Kabat.

In some embodiments, a modification comprises substitution of one or more amino acids that increases binding affinity of an IgG Fc domain or region to FcγRII and FcγRIIIA receptors. In some embodiments, a modification can be a substitution of T256, such as T256A, according to the EU index of Kabat. In some embodiments, a modification can be a substitution of K290, such as K290A, according to the EU index of Kabat.

In some embodiments, a modification comprises substitution of one or more amino acids that increases binding affinity of an IgG Fc domain or region to FcγRII receptor. In some embodiments, a modification can be a substitution of R255, such as R255A, according to the EU index of Kabat. In some embodiments, a modification can be a substitution of E258, such as E258A, according to the EU index of Kabat. In some embodiments, a modification can be a substitution of S267, such as S267A, according to the EU index of Kabat. In some embodiments, a modification can be a substitution of E272, such as E272A, according to the EU index of Kabat. In some embodiments, a modification can be a substitution of N276, such as N276A, according to the EU index of Kabat. In some embodiments, a modification can be a substitution of D280, such as D280A, according to the EU index of Kabat. In some embodiments, a modification can be a substitution of H285, such as H285A, according to the EU index of Kabat. In some embodiments, a modification can be a substitution of N286, such as N286A, according to the EU index of Kabat. In some embodiments, a modification can be a substitution of T307, such as T307A, according to the EU index of Kabat. In some embodiments, a modification can be a substitution of L309, such as L309A, according to the EU index of Kabat. In some embodiments, a modification can be a substitution of N315, such as N315 A, according to the EU index of Kabat. In some embodiments, a modification can be a substitution of K326, such as K326A, according to the EU index of Kabat. In some embodiments, a modification can be a substitution of P331, such as P331A, according to the EU index of Kabat. In some embodiments, a modification can be a substitution of S337, such as S337A, according to the EU index of Kabat. In some embodiments, a modification can be a substitution of A378, such as A378A, according to the EU index of Kabat. In some embodiments, a modification can be a substitution of E430, such as E430, according to the EU index of Kabat.

In some embodiments, a modification comprises substitution of one or more amino acids that increases binding affinity of an IgG Fc domain or region to FcγRII receptor and reduces the binding affinity to FcγRIIIA receptor. In some embodiments, a modification can be a substitution of H268, such as H268A, according to the EU index of Kabat. In some embodiments, a modification can be a substitution of R301, such as R301A, according to the EU index of Kabat. In some embodiments, a modification can be a substitution of K322, such as K322A, according to the EU index of Kabat.

In some embodiments, a modification comprises substitution of one or more amino acids that decreases binding affinity of an IgG Fc domain or region to FcγRII receptor but does not significantly affect the binding affinity to FcγRIIIA receptor. In some embodiments, a modification can be a substitution of R292, such as R292A, according to the EU index of Kabat. In some embodiments, a modification can be a substitution of K414, such as K414A, according to the EU index of Kabat.

In some embodiments, a modification comprises substitution of one or more amino acids that decreases binding affinity of an IgG Fc domain or region to FcγRII receptor and increases the binding affinity to FcγRIIIA receptor. In some embodiments, a modification can be a substitution of S298, such as S298A, according to the EU index of Kabat. In some embodiments, a modification can be substitution of S239, I332 and A330, such as S239D/I332E/A330L. In some embodiments, a modification can be substitution of S239 and I332, such as S239D/I332E.

In some embodiments, a modification comprises substitution of one or more amino acids that decreases binding affinity of an IgG Fc domain or region to FcγRIIIA receptor. In some embodiments, a modification can be substitution of F241 and F243, such as F241 S/F243S or F241I/F243I, according to the EU index of Kabat.

In some embodiments, a modification comprises substitution of one or more amino acids that decreases binding affinity of an IgG Fc domain or region to FcγRIIIA receptor and does not significantly affect the binding affinity to FcγRII receptor. In some embodiments, a modification can be a substitution of S239, such as S239A, according to the EU index of Kabat. In some embodiments, a modification can be a substitution of E269, such as E269A, according to the EU index of Kabat. In some embodiments, a modification can be a substitution of E293, such as E293A, according to the EU index of Kabat. In some embodiments, a modification can be a substitution of Y296, such as Y296F, according to the EU index of Kabat. In some embodiments, a modification can be a substitution of V303, such as V303A, according to the EU index of Kabat. In some embodiments, a modification can be a substitution of A327, such as A327G, according to the EU index of Kabat. In some embodiments, a modification can be a substitution of K338, such as K338A, according to the EU index of Kabat. In some embodiments, a modification can be a substitution of D376, such as D376A, according to the EU index of Kabat.

In some embodiments, a modification comprises substitution of one or more amino acids that increases binding affinity of an IgG Fc domain or region to FcγRIIIA receptor and does not affect the binding affinity to FcγRII receptor. In some embodiments, a modification can be a substitution of E333, such as E333A, according to the EU index of Kabat. In some embodiments, a modification can be a substitution of K334, such as K334A, according to the EU index of Kabat. In some embodiments, a modification can be a substitution of A339, such as A339T, according to the EU index of Kabat. In some embodiments, a modification can be substitution of S239 and I332, such as S239D/I332E, according to the EU index of Kabat.

In some embodiments, a modification comprises a substitution of one or more amino acids that increases binding affinity of an IgG Fc domain or region to FcγRIIIA receptor. In some embodiments, a modification can be substitution of L235, F243, R292, Y300 and P396, such as L235V/F243L/R292P/Y300L/P396L (IgGI VLPLL), according to the EU index of Kabat. In some embodiments, a modification can be substitution of S298, E333 and K334, such as S298A/E333 A/K334A, according to the EU index of Kabat. In some embodiments, a modification can be substitution of K246, such as K246F, according to the EU index of Kabat.

Other substitutions in an IgG Fc domain that affect its interaction with one or more Fcgamma receptors are disclosed in U.S. Pat. Nos. 7,317,091 and 8,969,526 (the disclosures of which are incorporated by reference herein).

In some embodiments, an IgG Fc domain or region comprises at least one amino acid substitution that reduces the binding affinity to FcRn, as compared to a wild-type or reference IgG Fc domain. In some embodiments, a modification can comprise a substitution at H435, such as H435A, according to the EU index of Kabat. In some embodiments, a modification can comprise a substitution at I253, such as I253A according to the EU index of Kabat. In some embodiments, a modification can comprise a substitution at H310, such as H310A according to the EU index of Kabat. In some embodiments, a modification can comprise substitutions at I253, H310 and H435, such as I253A/H310A/H435A according to the EU index of Kabat.

In some embodiments, a modification can comprise a substitution of one amino acid residue that increases the binding affinity of an IgG Fc domain for FcRn, relative to a wildtype or reference IgG Fc domain. In some embodiments, a modification can comprise a substitution at V308, such as V308P according to the EU index of Kabat. In some embodiments, a modification can comprise a substitution at M428, such as M428L according to the EU index of Kabat. In some embodiments, a modification can comprise a substitution at N434, such as N434A according to the EU index of Kabat or N434H according to the EU index of Kabat. In some embodiments, a modification can comprise substitutions at T250 and M428, such as T250Q and M428L according to the EU index of Kabat. In some embodiments, a modification can comprise substitutions at M428 and N434, such as M428L and N434S, N434A or N434H according to the EU index of Kabat. In some embodiments, a modification can comprise substitutions at M252, S254 and T256, such as M252Y/S254T/T256E according to the EU index of Kabat. In some embodiments, a modification can be a substitution of one or more amino acids selected from P257L, P257N, P257I, V279E, V279Q, V279Y, A281 S, E283F, V284E, L306Y, T307V, V308F, Q31 IV, D376V, and N434H. Other substitutions in an IgG Fc domain that affect its interaction with FcRn are disclosed in U.S. Pat. No. 9,803,023 (the disclosure of which is incorporated by reference herein).

In some embodiments, a MIC antibody or antigen binding portion thereof has a modified constant region (Fc region) or Fc domain that modifies complement-dependent cytotoxicity (CDC) activity. CDC is a cell-killing method that can be directed by antibodies. IgM is the most effective isotype for complement activation. IgG1 and IgG3 are also both very effective at directing CDC via the classical complement-activation pathway.

In some embodiments, an Fc region has modifications at one or more of amino acid positions E318, K320, K322, P329, and/or P331 of an IgG1, such as E318A, K320A, K322A, P329A and/or P331A, according to the EU Index of Kabat, that reduce CDC activity. In some embodiments, an Fc region has modifications at one or more of amino acid positions E430, E345 and S440 of an IgG1, according to the EU index of Kabat, such as one or more of E430G, E345K, E430S, E430F, E430T, E345Q, E345R, E345Y, S440Y and/or S440W, which increase CDC activity.

In various embodiments, MIC antibodies, antigen binding portions thereof and other binding agents can be produced in human, murine or other animal-derived cells lines. Recombinant DNA expression can be used to produce MIC antibodies, antigen binding portions thereof and other binding agents. This allows the production of MIC antibodies as well as a spectrum of MIC antigen binding portions and other binding agents (including fusion proteins) in a host species of choice. The production of MIC antibodies, antigen binding portions thereof and other binding agents in bacteria, yeast, transgenic animals and chicken eggs are also alternatives for cell-based production systems. The main advantages of transgenic animals are potential high yields from renewable sources.

In some embodiments, a MIC VH polypeptide having the amino acid sequence set forth in SEQ ID NO: 1 is encoded by a nucleic acid. In some embodiments, a MIC VL polypeptide having the amino acid sequence set forth in SEQ ID NO: 2 is encoded by a nucleic acid. In some embodiments, a MIC VH polypeptide having the amino acid sequence set forth in SEQ ID NO: 1 is encoded by a nucleic acid having the sequence set forth in SEQ ID NO:21. In some embodiments, a MIC VL polypeptide having the amino acid sequence set forth in SEQ ID NO: 2 is encoded by a nucleic acid having the sequence set forth in SEQ ID NO:22.

As used herein, the term "nucleic acid" or "nucleic acid sequence" or "polynucleotide sequence" or "nucleotide" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. In some embodiments, the nucleic acid can be a cDNA, e.g., a nucleic acid lacking introns.

Nucleic acid molecules encoding the amino acid sequence of a MIC antibody, antigen binding portion thereof as well as other binding agents can be prepared by a variety of methods known in the art. These methods include, but are not limited to, preparation of synthetic nucleotide sequences encoding of a MIC antibody, antigen binding portion or other binding agent(s). In addition, oligonucleotide-mediated (or site-directed) mutagenesis, PCR-mediated mutagenesis, and cassette mutagenesis can be used to prepare nucleotide sequences encoding a MIC antibody or antigen binding portion as well as other binding agents. A nucleic acid sequence encoding at least a MIC antibody, antigen binding portion thereof, binding agent, or a polypeptide thereof, as described herein, can be recombined with vector DNA in accordance with conventional techniques, such as, for example, blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, N Y, 1982 and 1989), and Ausubel et al., Current Protocols in Molecular Biology (John Wiley & Sons), 1987-1993, and can be used to construct nucleic acid sequences and vectors that encode a MIC antibody or antigen binding portion thereof or a VH or VL polypeptide thereof.

A nucleic acid molecule, such as DNA, is said to be "capable of expressing" a polypeptide if it contains nucleotide sequences that contain transcriptional and translational regulatory information and such sequences are "operably linked" to nucleotide sequences that encode the polypeptide. An operable linkage is a linkage in which the regulatory DNA sequences and the DNA sequence sought to be expressed (e.g., a MIC antibody or antigen binding portion thereof) are connected in such a way as to permit gene expression of a polypeptide(s) or antigen binding portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of a MIC antibody or antigen-binding portion thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of a MIC antibody or antigen binding portion thereof as described herein with a specified amino terminus sequence. Moreover, problems associated with retention of initiation codon-derived methionine residues in direct yeast (or bacterial) expression maybe avoided. (See, e.g., Sabin et al., 7 Bio/Technol. 705 (1989); Miller et al., 7 Bio/Technol. 698 (1989).) Any of a series of yeast gene expression systems incorporating promoter and termination elements from the actively expressed genes coding for glycolytic enzymes produced in large quantities when yeast are grown in medium rich in glucose can be utilized to obtain recombinant MIC antibodies or antigen-binding portions thereof. Known glycolytic genes can also provide very efficient transcriptional control signals. For example, the promoter and terminator signals of the phosphoglycerate kinase gene can be utilized.

Production of MIC antibodies or antigen-binding portions thereof in insects can be achieved, for example, by infecting an insect host with a baculovirus engineered to express a polypeptide by methods known to those of ordinary skill in the art. See Ausubel et al., 1987-1993.

In some embodiments, the introduced nucleic acid sequence (encoding a MIC antibody or antigen binding portion thereof or a polypeptide thereof) is incorporated into a plasmid or viral vector capable of autonomous replication in a recipient host cell. Any of a wide variety of vectors can be employed for this purpose and are known and available to those of ordinary skill in the art. See, e.g., Ausubel et al., 1987-1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Exemplary prokaryotic vectors known in the art include plasmids such as those capable of replication in *E. coli*. Other gene expression elements useful for the expression of DNA encoding MIC antibodies or antigen-binding portions thereof include, but are not limited to (a) viral transcription promoters and their enhancer elements, such as the SV40 early promoter. (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983). Immunoglobulin-encoding DNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin encoding nucleotide sequences, the transcriptional promoter can be, for example, human cytomegalovirus, the promoter enhancers can be cytomegalovirus and mouse/human immunoglobulin.

In some embodiments, for expression of DNA coding regions in rodent cells, the transcriptional promoter can be a viral LTR sequence, the transcriptional promoter enhancers can be either or both the mouse immunoglobulin heavy chain enhancer and the viral LTR enhancer, and the polyadenylation and transcription termination regions. In other embodiments, DNA sequences encoding other proteins are combined with the above-recited expression elements to achieve expression of the proteins in mammalian cells.

Each coding region or gene fusion is assembled in, or inserted into, an expression vector. Recipient cells capable of expressing the MIC variable region(s) or antigen binding portions thereof (e.g., a VH having the amino acid sequence set forth in SEQ ID NO:1 and/or a VL having the amino acid sequence set forth in SEQ ID NO:2 or a variant thereof as described herein) are then transfected singly with nucleotides encoding a MIC antibody or an antibody polypeptide or antigen-binding portion thereof, or are co-transfected with a polynucleotide(s) encoding VH and a VL chain coding regions. The transfected recipient cells are cultured under conditions that permit expression of the incorporated coding regions and the expressed antibody chains or intact antibodies or antigen binding portions are recovered from the culture.

In some embodiments, the nucleic acids containing the coding regions encoding a MIC antibody or antigen-binding portion thereof (e.g., a VH having the amino acid sequence set forth in SEQ ID NO:1 and/or a VL having the amino acid sequence set forth in SEQ ID NO:2 or a variant thereof as described herein) are assembled in separate expression vectors that are then used to co-transfect a recipient host cell. Each vector can contain one or more selectable genes. For example, in some embodiments, two selectable genes are used, a first selectable gene designed for selection in a bacterial system and a second selectable gene designed for selection in a eukaryotic system, wherein each vector has a set of coding regions. This strategy results in vectors which first direct the production, and permit amplification, of the nucleotide sequences in a bacterial system. The DNA vectors so produced and amplified in a bacterial host are subsequently used to co-transfect a eukaryotic cell, and allow selection of a co-transfected cell carrying the desired transfected nucleic acids (e.g., containing MIC antibody heavy and light chains). Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused nucleotide sequences encoding VH and VL chains can be assembled on the same expression vector.

For transfection of the expression vectors and production of the MIC antibodies or antigen binding portions thereof, the recipient cell line can be a Chinese Hamster ovary cell line (e.g., DG44) or a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells only produce immunoglobulins encoded by the transfected genes. Myeloma cells can be grown in culture or in the peritoneal cavity of a mouse, where secreted immunoglobulin can be obtained from ascites fluid.

An expression vector encoding a MIC antibody or antigen-binding portion thereof (e.g., a VH having the amino acid sequence set forth in SEQ ID NO:1 and/or a VL having the amino acid sequence set forth in SEQ ID NO:2 or a variant thereof as described herein) can be introduced into an appropriate host cell by any of a variety of suitable means, including such biochemical means as transformation, transfection, protoplast fusion, calcium phosphate-precipitation, and application with polycations such as diethylaminoethyl (DEAE) dextran, and such mechanical means as electroporation, direct microinjection and microprojectile bombardment. Johnston et al., 240 Science 1538 (1988), as known to one of ordinary skill in the art.

Yeast provides certain advantages over bacteria for the production of immunoglobulin heavy and light chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes polypeptides bearing leader sequences (i.e., pre-polypeptides). See, e.g., Hitzman et al., 11th Intl. Conf. Yeast, Genetics & Molec. Biol. (Montpelier, France, 1982).

Yeast gene expression systems can be routinely evaluated for the levels of production, secretion and the stability of antibodies, and assembled MIC antibodies and antigen binding portions thereof. Various yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. Another example is the translational elongation factor 1alpha promoter. A number of approaches can be taken for evaluating optimal expression plasmids for the expression of immunoglobulins in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or antigen binding portions thereof described herein, *E. coli* K12 strains such as *E. coli* W3110 (ATCC 27325), *Bacillus* species, enterobacteria such as *Salmonella typhimurium* or *Serratia marcescens*, and various *Pseudomonas* species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of MIC antibodies and antigen binding portions thereof in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin molecules including leader peptide removal, folding and assembly of VH and VL chains, glycosylation of the antibody molecules, and secretion of functional antibody and/or antigen binding portions thereof.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Exemplary eukaryotic cells that can be used to express immunoglobulin polypeptides include, but are not limited to, COS cells, including COS 7 cells; 293 cells, including 293-6E cells; CHO cells, including CHO—S and DG44 cells; PERC6™ cells (Crucell); and NSO cells. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, one or more MIC antibodies or antigen-binding portions thereof (e.g., a VH having the amino acid sequence set forth in SEQ ID NO:1 and/or a VL having the amino acid sequence set forth in SEQ ID NO:2 or a variant thereof as described herein) can be produced in vivo in an animal that has been engineered or transfected with one or more nucleic acid molecules encoding the polypeptides, according to any suitable method.

In some embodiments, an antibody or antigen-binding portion thereof (e.g., a VH having the amino acid sequence set forth in SEQ ID NO:1 and/or a VL having the amino acid sequence set forth in SEQ ID NO:2 or a variant thereof as described herein) is produced in a cell-free system. Non-limiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of the VH and VL chains (e.g., a VH having the amino acid sequence set forth in SEQ ID NO:1 and/or a VL having the amino acid sequence set forth in SEQ ID NO:2 or a variant thereof as described herein) in mammalian cells (see Glover, 1985). Various approaches can be followed to obtain intact antibodies. As discussed above, it is possible to co-express VH and VL chains and optionally the associated constant regions in the same cells to achieve intracellular association and linkage of VH and VL chains into complete tetrameric $H_2L_2$ antibodies or antigen-binding portions thereof. The co-expression can occur by using either the same or different plasmids in the same host. Nucleic acids encoding the VH and VL chains or antigen binding portions thereof (e.g., a VH having the amino acid sequence set forth in SEQ ID NO:1 and a VL having the amino acid sequence set forth in SEQ ID NO:2 or a variant thereof as described herein) can be placed into the same plasmid, which is then transfected into cells, thereby selecting directly for cells that express both chains. Alternatively, cells can be transfected first with a plasmid encoding one chain, for example the VL chain, followed by transfection of the resulting cell line with a VH chain plasmid containing a second selectable marker. Cell lines producing antibodies, antigen-binding portions thereof via either route could be transfected with plasmids encoding additional copies of peptides, VH, VL, or VH plus VL chains (e.g., a VH having the amino acid sequence set forth in SEQ ID NO:1 and/or a VL having the amino acid sequence set forth in SEQ ID NO:2 or a variant thereof as described herein) in conjunction with additional selectable markers to generate cell lines with enhanced properties, such as higher production of assembled MIC antibodies or antigen binding portions thereof or enhanced stability of the transfected cell lines.

Additionally, plants have emerged as a convenient, safe and economical alternative expression system for recombinant antibody production, which are based on large scale culture of microbes or animal cells. MIC binding antibodies or antigen binding portions can be expressed in plant cell culture, or plants grown conventionally. The expression in plants may be systemic, limited to sub-cellular plastids, or limited to seeds (endosperms). See, e.g., U.S. Patent Pub. No. 2003/0167531; U.S. Pat. Nos. 6,080,560; 6,512,162; WO 0129242. Several plant-derived antibodies have reached advanced stages of development, including clinical trials (see, e.g., Biolex, N.C.).

For intact antibodies, the variable regions (VH and VL) of the MIC antibodies (e.g., a VH having the amino acid sequence set forth in SEQ ID NO:1 and/or a VL having the amino acid sequence set forth in SEQ ID NO:2 or a variant thereof as described herein) are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). A MIC binding antibody can contain both light chain and heavy chain constant regions. The heavy chain constant region can include CH1, hinge, CH2, CH3, and, sometimes, CH4 regions. In some embodiments, the CH2 domain can be deleted or omitted.

Alternatively, techniques described for the production of single chain antibodies (see, e.g. U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989); which are incorporated by reference herein in their entireties) can be adapted to produce single chain antibodies that specifically bind to MIC. Single chain antibodies are formed by linking the heavy and light chain variable regions (e.g., having the amino acid sequences set forth in SEQ ID NO:1 and 2, or a variant thereof as described herein (e.g., optionally modified with from 1 to 8 amino acid substitutions, deletions and/or insertions)) of the Fv region via an amino acid bridge, resulting in a single chain polypeptide. Techniques for the assembly of functional Fv fragments in *E. coli* can also be used (see, e.g. Skerra et al., Science 242:1038-1041 (1988); which is incorporated by reference herein in its entirety).

Intact (e.g., whole) antibodies, their dimers, individual light and heavy chains, or antigen binding portions thereof can be recovered and purified by known techniques, e.g., immunoadsorption or immunoaffinity chromatography, chromatographic methods such as HPLC (high performance liquid chromatography), ammonium sulfate precipitation, gel electrophoresis, or any combination of these. See generally, Scopes, Protein Purification (Springer-Verlag, N.Y., 1982). Substantially pure MIC binding antibodies or antigen binding portions thereof of at least about 90% to 95% homogeneity are advantageous, as are those with 98% to 99% or more homogeneity, particularly for pharmaceutical uses. Once purified, partially or to homogeneity as desired, an intact MIC antibody or antigen binding portions thereof can then be used therapeutically or in developing and performing assay procedures, immunofluorescent staining, and the like. See generally, Vols. I & II Immunol. Meth. (Lefkovits & Pernis, eds., Acad. Press, N Y, 1979 and 1981).

Additionally, and as described herein, a MIC antibody or antigen binding portion thereof can be further optimized to decrease potential immunogenicity, while maintaining functional activity, for therapy in humans. In some embodiments, an optimized MIC binding antibody or antigen binding portion thereof is derived from a MIC antibody comprising (i) a heavy chain variable region having the amino acid sequence set forth in SEQ ID NO:1 and (ii) a light chain variable region having the amino acid sequence set forth in SEQ ID NO:2, wherein the heavy and light chain variable framework regions are optionally modified with from 1 to 8, 1 to 6, 1 to 4 or 1 to 2 conservative amino acid substitutions in the framework regions, wherein the CDRs of the heavy or light chain variable regions are not modified. In some embodiments, an optimized MIC binding antibody or antigen binding portion thereof is derived from a MIC binding antibody comprising (i) a heavy chain variable region having the amino acid sequence set forth in SEQ ID NO:1 and (ii) a light chain variable region having the amino acid sequence set forth in SEQ ID NO:2, wherein the heavy and light chain variable framework regions are optionally modified with from 1 to 8, 1 to 6, 1 to 4 or 1 to 2 amino acid substitutions, deletions or insertions in the framework regions, wherein the CDRs of the heavy or light chain variable regions are not modified. In this regard, functional activity means a MIC antibody or antigen binding portion thereof capable of displaying one or more known functional activities associated with a MIC binding antibody or antigen binding portion thereof comprising (i) a heavy chain variable region having the amino acid sequence set forth in SEQ ID NO:1 and (ii) a light chain variable region having the amino acid sequence set forth in SEQ ID NO:2. In any of these embodiments, the functional activity of the MIC binding antibody or antigen binding portion thereof includes specifically binding to MIC with a binding affinity greater than that of antibody B10G5. Additional functional activities include inhibition of MIC, and/or anti-cancer activity. Additionally, a MIC antibody or antigen binding portion thereof having functional activity means the polypeptide exhibits activity similar to, or better than, the activity of a reference antibody or antigen-binding portion thereof as described herein (e.g., a MIC binding antibody or antigen binding portion thereof comprising (i) a heavy chain variable region having the amino acid sequence set forth in SEQ ID NO:1 and (ii) a light chain variable region having the amino acid sequence set forth in SEQ ID NO:2 or a variant thereof, as described herein), as measured in a particular assay, such as, for example, a biological assay, with or without dose dependency. In the case where dose dependency does exist, it need not be identical to that of the reference antibody or antigen-binding portion thereof, but rather substantially similar to or better than the dose-dependence in a given activity as compared to the reference antibody or antigen-binding portion thereof as described herein (i.e., the candidate polypeptide will exhibit greater activity relative to the reference antibody).

Other aspects of the MIC antibodies and antigen binding portions thereof or other binding agents relate to compositions comprising active ingredients (i.e., including a MIC antibody or antigen-binding portion thereof or other binding agent as described herein or a nucleic acid encoding an antibody or antigen-binding portion thereof or other binding agent as described herein). In some embodiments, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on any particular formulation. Typically such compositions are prepared as injectable either as liquid solutions or suspensions; however, solid forms suitable for rehydration, or suspensions, in liquid prior to use can also be prepared. A preparation can also be emulsified or presented as a liposome composition. A MIC antibody or antigen binding portion thereof or other binding agent can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, a pharmaceutical composition can contain minor amounts of auxiliary substances such as wetting or emulsifying agents, pH buffering agents and the like which enhance or maintain the effectiveness of the active ingredient (e.g., a MIC antibody or antigen binding portion thereof). The pharmaceutical compositions as described herein can include pharmaceutically acceptable salts of the components therein. Pharmaceutically acceptable salts include the acid addition salts (formed with the free amino groups of a polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain the active ingredients (e.g., a MIC antibody and/or antigen binding portions thereof) and water, and may contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent that will be effective in the treatment of a particular disorder or condition will depend on the nature of the disorder or condition, and can be determined by standard clinical techniques.

In some embodiments, a pharmaceutical composition comprising a MIC antibody or antigen-binding portion thereof as described herein or a nucleic acid encoding a MIC antibody or antigen-binding portion thereof as described herein can be a lyophilisate.

In some embodiments, a syringe comprising a therapeutically effective amount of a MIC antibody or antigen binding portion thereof, or a pharmaceutical composition described herein is provided.

Treatment of Cancer

In some aspects, the MIC antibodies or antigen binding portions thereof or other binding agents as described herein can be used in a method(s) comprising administering a MIC antibody or antigen-binding portion thereof or other binding agent as described herein to a subject in need thereof. In some embodiments, the MIC binding antibody or antigen binding portion thereof comprises (i) a heavy chain variable region having the amino acid sequence set forth in SEQ ID NO:1, and (ii) a light chain variable region having the amino acid sequence set forth in SEQ ID NO:2. In some embodiments, the MIC binding antibody or antigen binding portion thereof comprises: (i) a heavy chain variable region having the amino acid sequence set forth in SEQ ID NO:1 and (ii) a light chain variable region having the amino acid sequence set forth in SEQ ID NO:2, wherein the heavy and light chain variable framework regions are optionally modified with from 1 to 8, 1 to 6, 1 to 4 or 1 to 2 conservative amino acid substitutions in the framework regions, wherein the CDRs of the heavy or light chain variable regions are not modified. In some embodiments, the MIC binding antibody or antigen binding portion thereof comprises: (i) a heavy chain variable region having the amino acid sequence set forth in SEQ ID NO:1 and (ii) a light chain variable region having the amino acid sequence set forth in SEQ ID NO:2, wherein the heavy and light chain variable framework regions are optionally modified with from 1 to 8, 1 to 6, 1 to 4 or 1 to 2 amino acid substitutions, deletions or insertions in the framework regions, wherein the CDRs of the heavy or light chain variable regions are not modified. In any of these embodiments, the MIC binding antibody specifically binds to MIC with a binding affinity greater than that of antibody B10G5.

In some embodiments, the subject is in need of treatment for a cancer and/or a malignancy. In some embodiments, the subject is in need of treatment for a MIC+ cancer or a MIC+ malignancy, such as for example an epithelial cell cancer, a MIC+ solid tumor or a MIC+ hematopoietic malignancy. In some embodiments, the method is for treating a subject having a MIC+ cancer or malignancy. In some embodiments, the method is for treating an epithelial cell cancer or a hematopoietic malignancy in a subject. In some embodiments, the method is for treating a MIC+ epithelial cell cancer or a MIC+ hematopoietic malignancy in a subject. As used herein, "epithelial cell cancer" refers to a cancer that develops from epithelial cells.

The methods described herein include administering a therapeutically effective amount of a MIC binding antibody or antigen binding portion thereof or other binding agent. As used herein, the phrase "therapeutically effective amount", "effective amount" or "effective dose" refers to an amount of the MIC antibody or antigen binding portion thereof or other binding agent as described herein that provides a therapeutic benefit in the treatment of, management of or prevention of relapse of a tumor or malignancy, e.g. an amount that provides a statistically significant decrease in at least one symptom, sign, or marker of a tumor or malignancy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The terms "cancer" and "malignancy" refer to an uncontrolled growth of cells which interferes with the normal functioning of the bodily organs and systems. A cancer or malignancy may be primary or metastatic, i.e. that is it has become invasive, seeding tumor growth in tissues remote from the original tumor site. A "tumor" refers to an uncontrolled growth of cells which interferes with the normal functioning of the bodily organs and systems. A subject that has a cancer is a subject having objectively measurable cancer cells present in the subject's body. Included in this definition are benign tumors and malignant cancers, as well as potentially dormant tumors and micro-metastases. Cancers that migrate from their original location and seed other vital organs can eventually lead to the death of the subject through the functional deterioration of the affected organs. Hematologic malignancies (hematopoietic cancers), such as leukemias and lymphomas, are able to e.g., out-compete the normal hematopoietic compartments in a subject, thereby leading to hematopoietic failure (in the form of anemia, thrombocytopenia and neutropenia) ultimately causing death.

Examples of cancers include, but are not limited to, carcinomas, lymphomas, blastomas, sarcomas, and leukemias. More particular examples of such cancers include, but are not limited to, basal cell carcinoma, biliary tract cancer, bladder cancer, bone cancer, brain and CNS cancer, breast cancer, cancer of the peritoneum, cervical cancer; choriocarcinoma, colon and rectum cancer (colorectal cancer), connective tissue cancer, cancer of the digestive system, endometrial cancer, esophageal cancer, eye cancer, cancer of the head and neck, gastric cancer (including gastrointestinal cancer and stomach cancer), glioblastoma (GBM), hepatic carcinoma, hepatoma, intra-epithelial neoplasm, kidney or renal cancer, larynx cancer, leukemia, liver cancer, lung cancer (e.g., small-cell lung cancer, non-small cell lung cancer, adenocarcinoma of the lung, and squamous carcinoma of the lung), lymphoma including Hodgkin's and non-Hodgkin's lymphoma, melanoma, myeloma, neuroblastoma, oral cavity cancer (e.g., lip, tongue, mouth, and pharynx), ovarian cancer, pancreatic cancer, prostate cancer, retinoblastoma, rhabdomyosarcoma, cancer of the respiratory system, salivary gland carcinoma, sarcoma, skin cancer, squamous cell cancer, testicular cancer, thyroid cancer, uterine or endometrial cancer, cancer of the urinary system, vulval cancer; as well as other carcinomas and sarcomas, as well as B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia), chronic lymphocytic leukemia (CLL), acute lymphoblastic leukemia (ALL), Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome.

In some embodiments, the carcinoma is selected from a solid tumor, including but not limited to, melanoma, prostate cancer, ovarian cancer, cervical cancer, breast cancer, lung cancer, colon cancer, kidney cancer, and head and neck cancer.

In some embodiments, the cancer or malignancy is MIC-positive (MIC+). As used herein, the terms "MIC-positive" or "sMIC+" are used to describe a cancer cell, a cluster of cancer cells, a tumor mass, or a metastatic cell that express MIC on the cell surface (membrane-bound MIC) and/or produce a sMIC protein that is released from the cancer cell(s). These terms are intended to encompass all cancer cells and/or tumor masses that shed all or part of the extracellular domain of a MIC protein into the intratumoral space or into the circulatory or lymphatic system; thus these cells may only display a MIC protein on its surface for a short time period—that is, the term encompasses cancer cells and tumor cells that shed sMIC protein or secret sMIC through exosomes or other mechanisms, regardless of whether detectable MIC protein remains present on their cell surface or not. However, any cancer cell or tumor that is capable of escaping innate immune rejection by shedding MIC is considered to be a "MIC-positive cancer" as that term is used herein. Some non-limiting examples of MIC-positive cancers include epithelial cell cancers and hematopoietic malignancies. In some embodiments, the MIC-positive cancer or malignancy can be a MIC-positive prostate cancer and/or metastasis thereof.

As used herein, a "subject" refers to a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, various cancers. In addition, the methods described herein can be used to treat domesticated animals and/or pets. A subject can be male or female. In certain embodiments, the subject is a human.

A subject can be one who has been previously diagnosed with or identified as suffering from a sMIC+ or MIC+ cancer and in need of treatment, but need not have already undergone treatment for the sMIC+ or MIC+ cancer. Alternatively, a subject can also be one who has not been previously diagnosed as having a sMIC+ or MIC+ cancer in need of treatment. A subject can be one who exhibits one or more risk factors for a condition or one or more complications related to a sMIC+ or MIC+ cancer or a subject who does not exhibit risk factors. A "subject in need" of treatment for a sMIC+ cancer particular can be a subject having that condition or diagnosed as having that condition. In other embodiments, a subject "at risk of developing" a condition refers to a subject diagnosed as being at risk for developing the condition (e.g., a sMIC+ or MIC+ cancer).

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, reduction in free sMIC levels in the subject, alleviation of one or more symptom(s), diminishment of extent of the deficit, stabilized (i.e., not worsening) state of a cancer or malignancy, delay or slowing of tumor growth and/or metastasis, and an increased lifespan as compared to that expected in the absence of treatment. As used herein, the term "administering," refers to providing a MIC binding antibody or antigen-binding portion thereof or other binding agent as described herein or a nucleic acid encoding the MIC antibody or antigen-binding portion thereof or other binding agent as described herein into a subject by a method or route which results in binding to the MIC binding antibody or antigen binding portion thereof or other binding agent to MIC. Similarly, a pharmaceutical composition comprising a MIC binding antibody or antigen-binding portion thereof or other binding agent as described herein or a nucleic acid encoding the MIC antibody or antigen-binding portion thereof or other binding agent as described herein disclosed herein can be administered by any appropriate route which results in an effective treatment in the subject.

The dosage ranges for a MIC binding antibody or antigen binding portion thereof depend upon the potency, and encompass amounts large enough to produce the desired effect e.g., reducing levels of MIC, slowing of tumor growth or a reduction in tumor size. The dosage should not be so large as to cause unacceptable adverse side effects. Generally, the dosage will vary with the age, condition, and sex of the subject and can be determined by one of skill in the art. The dosage can also be adjusted by the individual physician in the event of any complication. In some embodiments, the dosage ranges from 0.01 mg/kg body weight to 10 mg/kg body weight. In some embodiments, the dose range is from 0.05 mg/kg body weight to 5 mg/kg body weight. In some embodiments, the dosage ranges from 0.01 mg/kg body weight to 10 mg/kg body weight. In some embodiments, the dose range is from 0.05 mg/kg body weight to 5 mg/kg body weight. Alternatively, the dose range can be titrated to maintain serum levels between 1 μg/mL and 1000 ug/mL. For systemic administration, subjects can be administered a therapeutic amount, such as, e.g. 0.01 mg/kg, 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg or more.

Administration of the doses recited above can be repeated. In fact, to the extent that clearing of free or unbound MIC can promote immune attack on a tumor, cancer cell or malignant cell, long term administration is contemplated, e.g. first to treat the tumor, cancer or malignancy itself, and then to provide continued surveillance against the development of tumor cells that gain the ability to shed MIC. In a preferred embodiment, the doses recited above are administered weekly, biweekly, every three weeks or monthly for several weeks or months. The duration of treatment depends upon the subject's clinical progress and responsiveness to treatment.

In some embodiments, a dose can be from about 0.01 mg/kg to about 100 mg/kg. In some embodiments, a dose can be from about 0.01 mg/kg to about 25 mg/kg. In some embodiments, a dose can be from about 0.01 mg/kg to about 20 mg/kg. In some embodiments, a dose can be from about 0.01 mg/kg to about 15 mg/kg. In some embodiments, a dose can be from about 0.01 mg/kg to about 100 mg/kg. In some embodiments, a dose can be from about 0.01 mg/kg to about 25 mg/kg. In some embodiments, a dose can be from about 0.01 mg/kg to about 20 mg/kg. In some embodiments, a dose can be from about 0.01 mg/kg to about 15 mg/kg. In some embodiments, a dose can be from about 0.1 mg/kg to about 10 mg/kg. In some embodiments, a dose can be from about 1 mg/kg to about 100 mg/kg. In some embodiments, a dose can be from about 1 mg/kg to about 25 mg/kg. In some embodiments, a dose can be from about 1 mg/kg to about 20 mg/kg. In some embodiments, a dose can be from about 1 mg/kg to about 15 mg/kg. In some embodiments, a dose can be about 2 mg/kg. In some embodiments, a dose can be about 4 mg/kg. In some embodiments, a dose can be about 5 mg/kg. In some embodiments, a dose can be about 6 mg/kg. In some embodiments, a dose can be about 8 mg/kg. In some embodiments, a dose can be about 10 mg/kg. In some embodiments, a dose can be about 15 mg/kg. In some embodiments, a dose can be from about 100 mg/m$^2$ to about 700 mg/m$^2$. In some embodiments, a dose can be about 250 mg/m$^2$. In some embodiments, a dose can be about 375 mg/m$^2$. In some embodiments, a dose can be about 400 mg/m$^2$. In some embodiments, the dose can be about 500 mg/m$^2$.

In some embodiments, a dose can be administered intravenously. In some embodiments, an intravenous administration can be an infusion occurring over a period of from about 10 minute to about 4 hours. In some embodiments, an intravenous administration can be an infusion occurring over a period of from about 30 minutes to about 90 minutes.

In some embodiments, a dose can be administered weekly. In some embodiments, a dose can be administered bi-weekly. In some embodiments, a dose can be administered about every 2 weeks. In some embodiments, a dose can be administered about every 3 weeks. In some embodiments, a dose can be administered every three weeks. In some embodiments, a dose can be administered every four weeks.

In some embodiments, a total of from about 2 to about 10 doses are administered to a subject. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, a total of 9 doses are administered. In some embodiments, a total of 10 doses are administered. In some embodiments, a total of more than 10 doses are administered.

Pharmaceutical compositions containing a MIC binding antibody or antigen binding portion thereof or other MIC binding agent can be administered in a unit dose. The term "unit dose" when used in reference to a pharmaceutical composition refers to physically discrete units suitable as unitary dosage for the subject, each unit containing a predetermined quantity of active material (e.g., a MIC binding antibody or antigen binding portion thereof), calculated to produce the desired therapeutic effect in association with the required physiologically acceptable diluent, i.e., carrier, or vehicle.

In some embodiments, a MIC binding antibody or an antigen binding portion thereof, or a pharmaceutical composition of either or both of these, is administered with an immunotherapy. As used herein, "immunotherapy" refers to therapeutic strategies designed to induce or augment the subject's own immune system to fight the cancer or malignancy. Examples of an immunotherapy include, but are not limited to, adoptive cell therapies (e.g., autologous NK cells, allogeneic NK cells, autologous T cells, CAR modified T cells and CAR modified NK cells), antibodies such as check point inhibitors, and antibodies disturbing metabolic signaling, immune cytokines, such as gamma-chain family cytokines IL-2, IL15 and variants thereof, chemotoxins, radiation therapy, and epigenetic modifiers. See, e.g., Rohaan et al., Virchows Archiv 474:449-461 (2019); Magalhaes et al., Expert Opinion on Biological Therapy 19:8, 811-827 (2019) and Ott et al., 2019 ASCO Educational Book, Developmental Immunotherapy and Tumor Immunobiology, e70-78 (2020), the disclosures of which are incorporated by reference herein.

In some embodiments, the adoptive cell therapy is a T cell therapy, such as CAR T cell therapy in which T cells are removed from the subject blood, genetically modified to express a chimeric antigen receptor against a suitable target on a cancer cell) and then re-administered to the subject. See, e.g., WO2019/018603; WO2019/090003; WO2020/033927; WO2019089969; WO2015/164675; WO2016064929; WO2019/032929; WO2016/115559; WO2016/033570; WO2014/130657; WO2016028896; WO2015/090230; and WO2014/153270.

In some embodiments, the adoptive cell therapy is a cell therapy in which PBMCs are removed from the subject blood, primed to respond to a particular antigen, and then re-administered to the subject (e.g., Sipuleucel-T). (See, e.g., WO2001/039594; WO2001/074855; and WO1999/063050.)

In some embodiments, the adoptive cell therapy is an NK cell therapy. NK cells can be engineered to express a chimeric antigen receptor against a suitable target on a cancer cell and then the engineered NK cells are administered to a subject. (See, e.g., WO2006/103569; WO2018/165291; WO2016/201304; WO2017/100709; WO2019/028337; WO2016/176651 and WO2018/183385)

In some embodiments, the immunotherapy involves administration of a checkpoint inhibitor. In some embodiments, the checkpoint inhibitor is selected from inhibitors or CTLA-4, PD-1, PD-L1, PD-L2, B7-H3, B7-H4, BMA, HVEM, TIM3, GAL9, LAG3, VISTA, KIR, LILRB1, LILRB2, CD47, CD137, CD70, 2B4, CD160, TIGIT, CGEN-15049, CHK1, CHK2, SIGLEC-15, NKG2A, CD39, CD73, A2AR, and A2BR. In some embodiments, the immune checkpoint inhibitors include agents that inhibit CTLA-4, PD-1, PD-L1, and the like. Suitable anti-CTLA-4 therapy agents, include, for example, anti-CTLA-4 antibodies, human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, ipilimumab, tremelimumab, anti-CTLA-4 adnectins, anti-CTLA-4 domain antibodies, single chain anti-CTLA-4 mAbs, heavy chain anti-CTLA-4 mAbs, light chain anti-CTLA-4 mAbs, inhibitors of CTLA-4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP1212422B1. Additional anti-CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., Proc. Natl. Acad. Sci. USA, 95(17): 10067-10071 (1998); Camacho et al., J. Clin. Oncology, 22(145): Abstract No. 2505 (2004) (antibody CP-675206); Mokyr et al., Cancer Res, 58:5301-5304 (1998), U.S. Pat. Nos. 5,977,318, 6,682,736, 7,109,003, and 7,132,281.

Suitable anti-PD-1 and anti-PD-L1 therapy agents, include, for example, anti-PD-1 and anti-PD-L1 antibodies, human anti-PD-1 and anti-PD-L1 antibodies, mouse anti-PD-1 and anti-PD-L1 antibodies, mammalian anti-PD-1 and anti-PD-L1 antibodies, humanized anti-PD-1 and anti-PD-L1 antibodies, monoclonal anti-PD-1 and anti-PD-L1 antibodies, polyclonal anti-PD-1 and anti-PD-L1 antibodies, chimeric anti-PD-1 and anti-PD-L1 antibodies, anti-PD-1 adnectins and anti-PD-L1 adnectins, anti-PD-1 domain antibodies and anti-PD-L1 domain antibodies, single chain anti-PD-1 mAbs and single chain anti-PD-L1 mAbs, heavy chain anti-PD-1 mAbs and heavy chain anti-PD-L1 mAbs, and light chain anti-PD-1 mAbs and light chain anti-PD-L1 mAbs. In specific embodiments, anti-PD-1 therapy agents include nivolumab, pembrolizumab, pidilizumab, MED10680, and combinations thereof. In other specific embodiments, anti-PD-L1 therapy agents include atezolizumab, BMS-936559, MED14736, MSB0010718C, and combinations thereof.

Suitable anti-PD-1 and anti-PD-L1 antibodies are also described in Topalian, et al., Immune Checkpoint Blockade: A Common Denominator Approach to Cancer Therapy, Cancer Cell 27: 450-61 (Apr. 13, 2015), incorporated herein by reference in its entirety.

In some embodiments, the checkpoint inhibitor is Ipilimumab (Yervoy®), Nivolumab (Opdivo®), Pembrolizumab (Keytruda®), Atezolizumab (Tecentriq®), Avelumab (Bavencio®), or Durvalumab (Imfinzie).

In some embodiments, provided is a method of improving treatment outcome in a subject receiving immunotherapy. The method generally includes administering an effective amount of an immunotherapy to the subject having cancer; and administering a therapeutically effective amount of a binding agent or a pharmaceutical composition thereof to the subject, wherein the binding agent specifically binds to circulating MIC; wherein the treatment outcome of the subject is improved, as compared to administration of the immunotherapy alone. In some embodiments, the binding agent comprises (i) a heavy chain variable region having the amino acid sequence set forth in SEQ ID NO:1, and (ii) a light chain variable region having the amino acid sequence set forth in SEQ ID NO:2, wherein the heavy and light chain framework regions are optionally modified with from 1 to 8 amino acid substitutions, deletions or insertions in the framework regions, wherein the binding agent specifically binds to MIC with a binding affinity greater than that of antibody B10G5. In some embodiments, the binding agent comprises (i) a heavy chain variable region having the amino acid sequence set forth in SEQ ID NO:1, and (ii) a light chain variable region having the amino acid sequence set forth in SEQ ID NO:2, wherein the binding agent specifically binds to MIC. In some embodiments, the binding agent is an antibody or an antigen-binding portion thereof. In some embodiments, the binding agent is a monoclonal antibody, a Fab, a Fab', an F(ab'), an Fv, a disulfide linked Fc, a scFv, a single domain antibody, a diabody, a bi-specific antibody, or a multi-specific antibody.

In some embodiments, the improved treatment outcome is an objective response selected from stable disease, a partial response or a complete response as determined by standard medical criteria for the cancer being treated. In some embodiments, the improved treatment outcome is reduced tumor burden. In some embodiments, the improved treatment outcome is progression-free survival or disease-free survival.

In some embodiments, the methods further administering a MIC antibody or antigen binding portion thereof at least four weeks, at least six weeks or at least 8 weeks after administration of chemotherapy or other treatment that impairs the immune system by depleting endogenous NK cells or T cells or their precursors. In some such embodiments, the chemotherapy or treatment is selected from the group consisting of: radiation therapy, or chemotherapy. Non-limiting examples of chemotherapeutic agents can include alkylating agents such as thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin;

spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

By "radiation therapy" is meant the use of directed gamma rays or beta rays to induce sufficient damage to a cell so as to limit its ability to function normally or to destroy the cell altogether.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

NONLIMITING EXEMPLARY EMBODIMENTS

The present invention is further illustrated by the following embodiments which should not be construed as limiting.

1. A binding agent, comprising: (i) a heavy chain variable (VH) region having the amino acid sequence set forth in SEQ ID NO:1, and (ii) a light chain variable (VL) region having the amino acid sequence set forth in SEQ ID NO:2, wherein the heavy and light chain framework regions are optionally modified with from 1 to 8 amino acid substitutions, deletions or insertions in the framework regions.

2. A binding agent, comprising: (i) a heavy chain variable region having the amino acid sequence set forth in SEQ ID NO:1, and (ii) a light chain variable region having the amino acid sequence set forth in SEQ ID NO:2.

3. A binding agent comprising a heavy chain variable (VH) region and a light chain variable (VL) region, wherein the VH region comprises a complementarity determining region HCDR1 having the amino acid sequence set forth in SEQ ID NO:11, a HCDR2 having the amino acid sequence set forth in SEQ ID NO:12, and a HCDR3 having the amino acid sequence set forth in SEQ ID NO:13, and wherein the VL region comprises a LCDR1 having the amino acid sequence set forth in SEQ ID NO:14, a LCDR2 having the amino acid sequence set forth in SEQ ID NO:15, and a LCDR3 having the amino acid sequence set forth in SEQ ID NO: 16, and wherein the VH and VL regions each comprise a humanized framework region.

4. The binding agent of embodiment 3, wherein the humanized VH framework region is derived from a human germline gene having the amino acid sequence set forth in IMGT IGHV4-59*11 (SEQ ID NO:29) and IGHJ4*01 (SEQ ID NO:30) or IGHV4-30-4*01 (SEQ ID NO:31) and IGHJ4*01 (SEQ ID NO:30).

5. The binding agent of embodiments 3 or 4, wherein the humanized VL framework region is derived from a human germline gene having the amino acid sequence set forth in IMGT IGKV1-NL1*01 (SEQ ID NO:32) and IMGT IGKJ1*01 (SEQ ID NO:33), IMGT IGKV1-33*01 (SEQ ID NO:34) and IMGT IGKJ1*01 (SEQ ID NO:33) or IMGT IGKV1-5*01 (SEQ ID NO:35) and IMGT IGKJ1*01 (SEQ ID NO:33).

6. The binding agent of any one of embodiments 1 to 5, wherein the binding agent specifically binds to MIC.

7. The binding agent of any one of embodiments 1 to 6, wherein the binding agent is an antibody or an antigen-binding portion thereof.

8. The binding agent of embodiment 7, wherein the binding agent is a monoclonal antibody, a Fab, a Fab', a F(ab'), an Fv, a disulfide linked Fc, an scFv, a single domain antibody, a diabody, a bi-specific antibody, or a multi-specific antibody.

9. The binding agent of any one of the preceding embodiments, wherein the heavy chain variable region further comprises a heavy chain constant region.

10. The binding agent of embodiment 9, wherein heavy chain constant region is of the IgG isotype.

11. The binding agent of embodiment 10, wherein the heavy chain constant region is an IgG1 constant region.

12. The binding agent of embodiment 10, wherein the heavy chain constant region is an IgG4 constant region.

13. The binding agent of embodiment 11, wherein the heavy chain variable and constant regions have the amino acid sequence set forth in SEQ ID NO: 3.

14. The binding agent of any one of the preceding embodiments, wherein the light chain variable region further comprises a light chain constant region.

15. The binding agent of embodiment 14, wherein the light chain constant region is of the kappa isotype.

16. The binding agent of embodiment 15, wherein the light chain variable and constant regions have the amino acid sequence set forth in SEQ ID NO:4.

17. The binding agent of any one of embodiments 9 to 16, wherein the heavy chain constant region further comprises at least amino acid modification that increases binding affinity to human FcgammaRIII.

18. The binding agent of any one of embodiments 9 to 17, wherein the heavy chain constant region further comprises at least one amino acid modification that reduces binding to one or more Fcgamma receptors.

19. The binding agent of any one of embodiment 9 to 17, wherein the heavy chain constant region further comprises at least one amino acid modification that increases CDC activity.

20. The binding agent of any one of the embodiments, wherein the binding agent is mono-specific.

21. The binding agent of any one of embodiments 1 to 20, wherein the binding agent is bivalent.

22. The binding agent of embodiment 21, wherein the binding agent comprises a second binding domain and the binding agent is bispecific.

23. The binding agent of any one of embodiments 1 to 22, wherein the binding agent specifically binds to soluble MIC (sMIC).

24. The binding agent of any one of embodiments 1 to 23, wherein the binding agent specifically binds to MIC with a binding affinity greater than that of antibody B10G5.

25. A pharmaceutical composition comprising the binding agent of any of the preceding embodiments and a pharmaceutically acceptable carrier.

26. A nucleic acid encoding a heavy chain variable region having the amino acid sequence set forth in SEQ ID NO:1, optionally having the nucleic acid sequence set forth in SEQ ID NO:21.

27. A nucleic acid encoding a light chain variable region having the amino acid sequence set forth in SEQ ID NO:2, optionally having the nucleic acid sequence set forth in SEQ ID NO:22.

28. A nucleic acid encoding the binding agent of any one of embodiments 1 to 24, optionally having the nucleic acid sequences set forth in SEQ ID NO:21 and SEQ ID NO:22.

29. A vector comprising the nucleic acid of any one of embodiments 26 to 28.

30. A cell line comprising the nucleic acid of any one of embodiments 26 to 28 or the vector of embodiment 29.

31. A method of treating a MIC+ cancer, comprising administering to a subject in need thereof a therapeutically effective amount of the binding agent of any one of embodiments 1 to 24 or the pharmaceutical composition of embodiment 25.

32. The method of embodiment 31, wherein the cancer is a carcinoma, a sarcoma, a neuroendocrine tumor, or a hematologic malignancy.

33. The method of embodiment 33, wherein the cancer is a carcinoma.

34. The method of embodiment 33, wherein the carcinoma is selected from prostate, ovarian, cervical, breast, lung, colon, and head and neck cancer.

35. The method of embodiment 32, wherein the cancer is a hematologic malignancy.

36. The method of embodiment 33, wherein the hematologic malignancy is a lymphoma or multiple myeloma.

37. The method of any one of embodiments 31 to 36, further comprising administering an immunotherapy to the subject.

38. The method of embodiment 37, wherein the immunotherapy comprises an adoptive cell therapy or a checkpoint inhibitor.

39. The method of embodiment 38, wherein the immunotherapy comprises an adoptive cell therapy.

40. The method of embodiment 39, wherein the adoptive cell therapy is selected from autologous NK cells, allogeneic NK cells, autologous T cells, CAR modified T cells and CAR modified NK cells.

41. The method of embodiment 38, wherein the immunotherapy comprises a checkpoint inhibitor.

42. The method of embodiment 41, wherein the checkpoint inhibitor is selected from an antibody that specifically binds to human PD-1, human PD-L1, or human CTLA4.

43. The method of embodiment 42, wherein the checkpoint inhibitor is pembrolizumab, nivolumab, cemiplimab or ipilimumab.

44. The method of any one of embodiments 31 to 43, wherein chemotherapy is not administered to the subject for at least four weeks prior to the administration of the binding agent.

45. The method of any one of embodiments 31 to 44, wherein the binding agent is administered intravenously.

46. The method of any one of embodiments 31 to 45, wherein the binding agent is administered in a dose of about 0.1 mg/kg to about 100 mg/kg.

47. A method of reducing levels of circulating sMIC in a subject having cancer, comprising administering a therapeutically effective amount of the binding agent of any one of embodiments 1 to 24 or the pharmaceutical composition of embodiment 25.

48. The method of embodiment 47, wherein the cancer is a carcinoma, a sarcoma, a neuroendocrine tumor, or a hematologic malignancy.

49. The method of embodiment 48, wherein the cancer is a carcinoma.

50. The method of embodiment 49, wherein the carcinoma is selected from prostate, ovarian, cervical, breast, lung, colon, and head and neck cancer.

51. The method of embodiment 48, wherein the cancer is a hematologic malignancy.

52. The method of embodiment 51, wherein the hematologic malignancy is a lymphoma or multiple myeloma.

53. A method of improving treatment outcome in a subject receiving immunotherapy, comprising:
  a. administering an effective amount of an immunotherapy to the subject having cancer; and
  b. administering a therapeutically effective amount of the binding agent of any one of embodiments 1 to 24 or the pharmaceutical composition of embodiment 25 to the subject, wherein the binding agent specifically binds to MIC;
  wherein the treatment outcome of the subject is improved, as compared to administration of the immunotherapy alone.

54. The method of embodiment 53, wherein the improved treatment outcome is an objective response selected from stable disease, a partial response or a complete response.

55. The method of embodiment 53, wherein the improved treatment outcome is reduced tumor burden.

56. The method of embodiment 53, wherein the improved treatment outcome is progression-free survival or disease-free survival.

57. The method of embodiment 53, wherein the immunotherapy is an adoptive cell therapy or a checkpoint inhibitor.

58. The method of embodiment 57, wherein the immunotherapy is an adoptive cell therapy.

59. The method of embodiment 58, wherein the adoptive cell therapy comprises autologous NK cells, allogeneic NK cells, autologous T cells, CAR modified T cells and CAR modified NK cells.

60. The method of embodiment 57, wherein the immunotherapy is a checkpoint inhibitor.

61. The method of embodiment 60, wherein the checkpoint inhibitor comprises an antibody that specifically binds to human PD-1, human PD-L1, or CTLA4.

62. The method of embodiment 61, wherein the checkpoint inhibitor is pembrolizumab, nivolumab, cemiplimab or ipilimumab.

63. The method of any one of embodiments 53 to 62, wherein chemotherapy is not administered to the subject for at least four weeks prior to the administration of the binding agent.

64. The method of any one of embodiments 53 to 63, wherein the binding agent is administered intravenously.

65. The method of any one of embodiment 53 to 64, wherein the binding agent is administered in a dose of about 0.1 mg/kg to about 10 mg/kg.

66. Use of the binding agent of any one of embodiments 1 to 24 or the pharmaceutical composition of embodiment 25 for the treatment of MIC+ cancer in a subject.

67. Use of the binding agent of any one of embodiments 1 to 24 or the pharmaceutical composition of embodiment 25 for the treatment of MIC+ cancer in a subject receiving immunotherapy.

68. The binding agent of any one of embodiments 1 and 3 to 24, wherein the VH is selected from a heavy chain variable region having the amino acid sequence set forth in SEQ ID NOs: 1, 23 and 24 and the VL is selected from a light chain variable region having the amino acid sequence set forth in SEQ ID NO:2, 25, and 26.

69. The binding agent of embodiment 68, wherein the VH has the amino acid sequence set forth in SEQ ID NO:24 and the VL has the amino acid sequence set forth in SEQ ID NO:2.

EXAMPLES

Example 1: Generation of a Humanized Antibody

The following example describes the preparation of humanized versions of antibody B10G5. Three humanized light chains and three humanized heavy chains were designed based on two different heavy and light chain human acceptor frameworks. The first humanized chain for each parental chain utilizes a first framework and contains the most human sequence with minimal parental antibody framework sequence (designated humanized HC 1, LC 1). The second humanized chain for each parental chain uses the same framework as before but contains additional parental sequences (designated humanized HC 2, LC 2). The third humanized chain for each utilizes the second respective framework and, similar to HC 2/LC 2, also contains additional parental sequences fused with the human framework (designated humanized HC 3, LC 3).

The light and heavy humanized chains were then ready to be combined to create variant fully humanized antibodies. All possible combinations of humanized light and heavy chains were tested for their expression level and for binding affinity test, as described in the following examples.

Full-length antibody genes were constructed by first synthesizing the variable region sequences. The sequences were optimized for expression in mammalian cells. These variable region sequences were then cloned into expression vectors that already contain human Fc domains; for the heavy chain, the IgG1 constant region was utilized as requested. In addition, for comparison, the heavy and light chains of the parental antibody were constructed as full-length chimeric chains using the same backbone Fc sequences. The antibodies were identified as set forth in the following Table 1.

TABLE 1

Humanized Antibody Combinations

| Antibody Chain | Parental HC | Humanized HC1 | Humanized HC2 | Humanized HC3 |
|---|---|---|---|---|
| Parental LC | Ab-J | | | |
| Humanized LC1 | | Ab-A | Ab-D | Ab-B |
| Humanized LC2 | | Ab-H | Ab-C | Ab-E |
| Humanized LC3 | | Ab-I | Ab-K | Ab-G |

Example 2: Evaluation of Humanized Antibodies in Small Scale Production

All 9 humanized antibodies underwent 0.01 liter small scale production. The B10G5 antibody was also scaled-up for direct comparison. Plasmids for the indicated heavy and light chains were transfected into HEK293 cells cultured in suspension using chemically defined media in the absence of serum. Five days after transfection, the conditioned media from each production run was collected and clarified. Antibodies in the conditioned media were purified using MabSelect SuRe™ Protein A medium (GE Healthcare). The final yields are provided below (Table 2).

TABLE 2

Antibody Yield (mg) in Small Scale Production

| Antibody Chain | Parental HC | Humanized HC1 | Humanized HC2 | Humanized HC3 |
|---|---|---|---|---|
| Parental LC | 0.99 (Ab-J) | | | |
| Humanized LC1 | | 1.95 (Ab-A) | 2.5 (Ab-D) | 2.25 (Ab-B) |
| Humanized LC2 | | 2.97 (Ab-H) | 3.19 (Ab-C) | 2.47 (Ab-E) |
| Humanized LC3 | | 2.88 (Ab-I) | 3.11 (Ab-K) | 3.45 (Ab-G) |

CE-SDS analysis under reducing conditions was performed on the antibodies using a LabChip GXII (Perkin Elmer) and the resulting electropherograms were analyzed. Discrete peaks of heavy and light chains were observed for the purified humanized antibodies; peak heights [or area under the curve] for the heavy and light chains were similar. Antibodies C (HC2/LC2) and K (HC2/LC3) produced the greatest antibody yield.

Example 3: Binding Affinity Testing of the Humanized Antibodies

Figure 1:
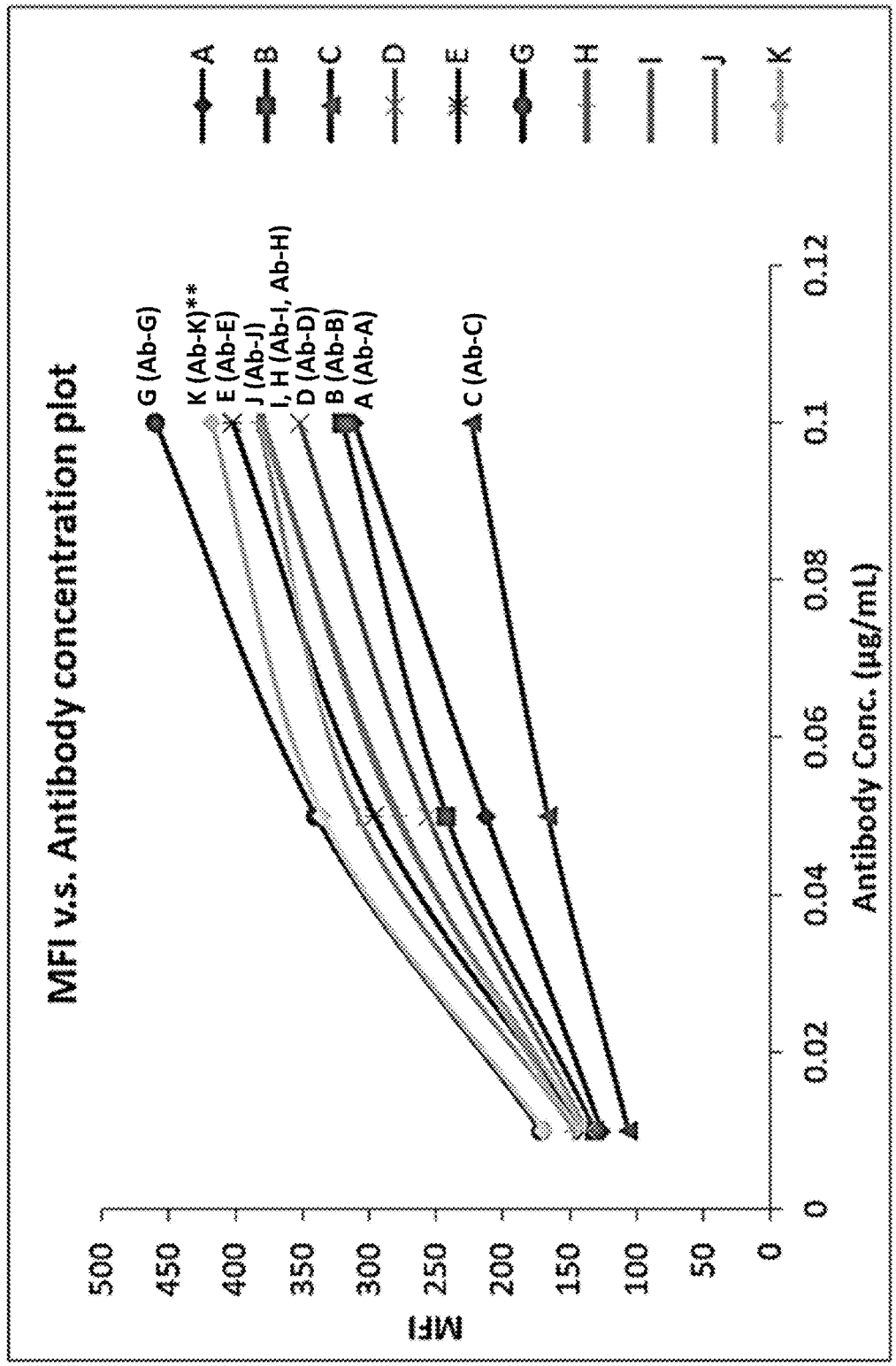
FIG. 1 shows an analysis of binding affinity by FACS of humanized variants of antibody B10G5 (attached to a human IgG1 Fc region). Two humanized variants, antibody G and antibody K, exhibited a higher mean fluorescence intensity (MFI) than antibody J (Ab-J; a B10G5 chimeric antibody that is composed on the F(ab)$_2$ of murine B10G5 antibody and the human IgG1 Fc domain).

The purified antibodies from Example 2 were analyzed for binding affinity by FACS on human prostate tumor cell line M12. Three different antibody concentrations were tested (0.1 ug/mL, 0.05 ug/mL and 0.01 ug/mL). To compare binding affinity, the MFI for each antibody at each concentration was determined and the results were plotted as shown in FIG. 1. From top to bottom at the 0.1 ug/mL concentration, the antibodies are Ab-G, Ab-K, Ab-E, Ab-J, Ab-I and Ab-H (overlapping), Ab-D, Ab-B, Ab-A and Ab-C. Surprisingly, two antibodies, Ab-G and Ab-K, had a higher MFI than antibody J (chimeric B10G5 having a human IgG1 Fc region).

Example 4: BLI Analysis of Antibody K by BLI

Figure 2A:
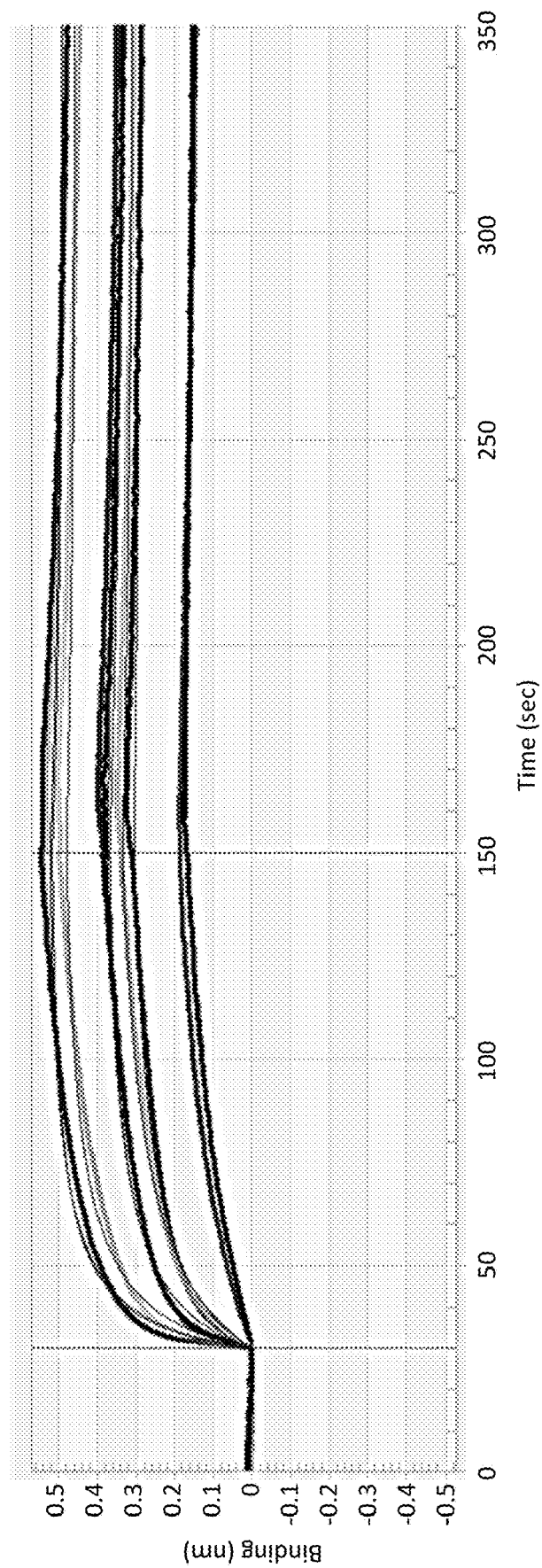
FIGS. 2A-2B show that antibody B10G5 (FIG. 2A) has a lower (weaker) binding affinity than antibody K (Ab-K.
Figure 2B:
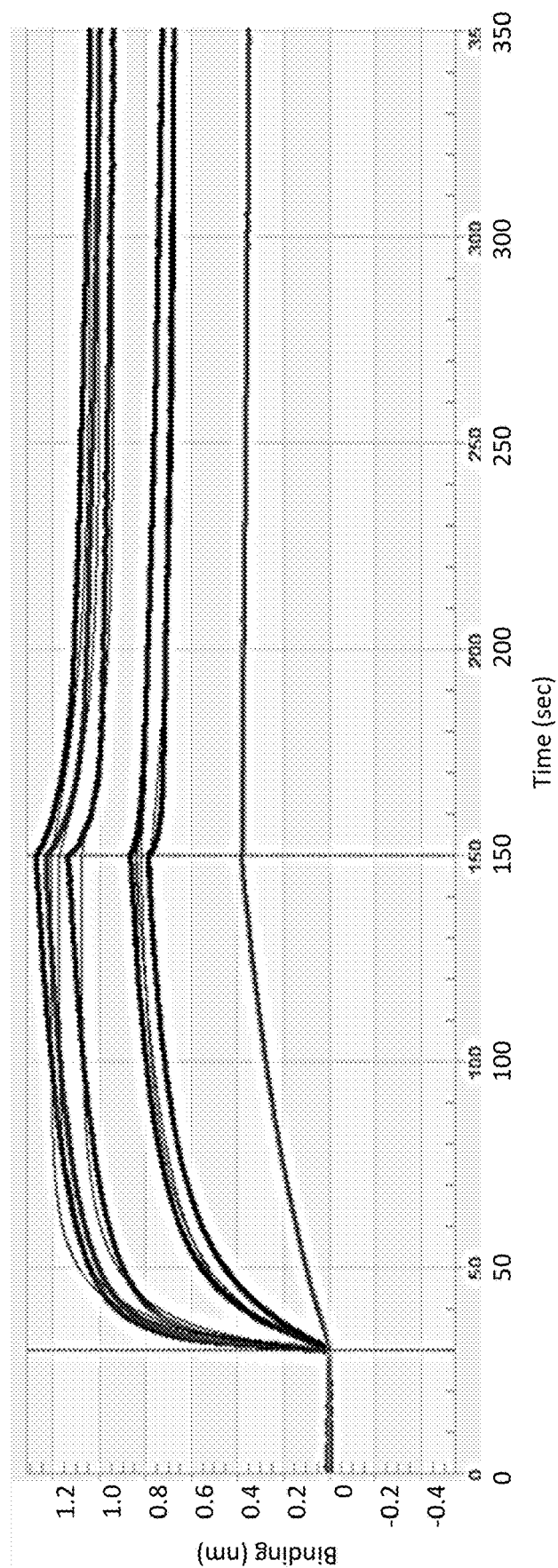

Bio-layer interferometry (BLI) was performed using Octet Red96 (ForteBio) generally as described by Kamat and Rafique, Analytical Biochemistry 536: 16-31 (2017). Antibody samples, Ab-K and Ab-J (chimeric B10G5), were captured on kinetic grade biosensors. The loaded biosensors were then dipped into a dilution series of samples containing antigen (MICB) serially diluted in PBS buffer with 0.1% BSA, 0.02% Tween-20, pH 7.2. Association was observed for 150 seconds followed by 200 seconds of dissociation. Duplicate injections of the same antigen concentration showed a good overlap. Kinetic analysis was performed using a 1:1 binding model and global fitting with mass transport limitation using the Scrubber software. Referring to FIGS. 2A-2B, Ab-K (FIG. 2B) had a higher affinity (Kd=7.2 nM) than that of chimeric antibody B10G5 (Ab-J, Kd=12.1 nM) (FIG. 2A).

Example 5: NK Cell Cytotoxicity Assay

The ability to antibody K to stimulate NK cell cytotoxicity was determined. NK cells were negatively selected from healthy donor PBMCs using isolation kits from Stem Cell Technologies (Vancouver, BC, Canada). Purified NK cells were activated with IL-2 (1000 U/mL) for 18 h before they were used for cytotoxicity assays against UC1 tumor cells or PL-12 cells that were pre-incubated with 10 ug/ml of control human IgG, antibody Ab-J (chimeric B10G5 having a human IgG1 Fc region), or antibody K (Ab-K) at 37° C. for 30 min. NK cell-mediated cytotoxicity was determined using standard 4 h 51 Cr release assay (Jewett A. et al., Hum. Immunol. 2003; 64:505-520). Specifically, NK cells were co-incubated with 51 Cr-labeled UC1 or PL12 cells at 10:1 ratio for 4h in a cell culture incubator. After 4h incubation, the supernatants were harvested from each sample and counted on a gamma counter. The percentage specific cytotoxicity was calculated using the formula: % cytotoxicity=(Experimental cpm−spontaneous cpm)/(total cpm−spontaneous cpm). The NK cell killing activity was expressed as lytic units $30/10^6$ cells that was determined using inverse numbers of NK cells required to lyse 30% of the target cells×100. Five replicates of each condition were included in the experiments.

Figure 3A:
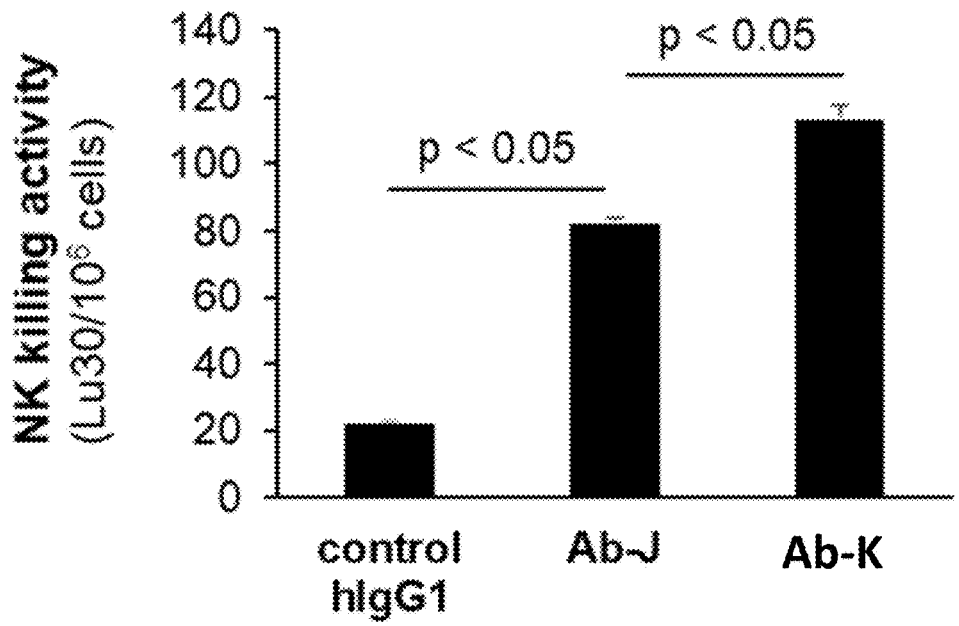
FIGS. 3A-3B show that antibody K (Ab-K) demonstrates higher activity than Ab-J (the chimeric B10G5) in enhancing IL-2 activated primary NK cell killing of MIC$^+$ thyroid oncocytoma UC1 tumor cells (FIG. 3A); and pancreatic PL12 cells (FIG. 3B).
Figure 3B:
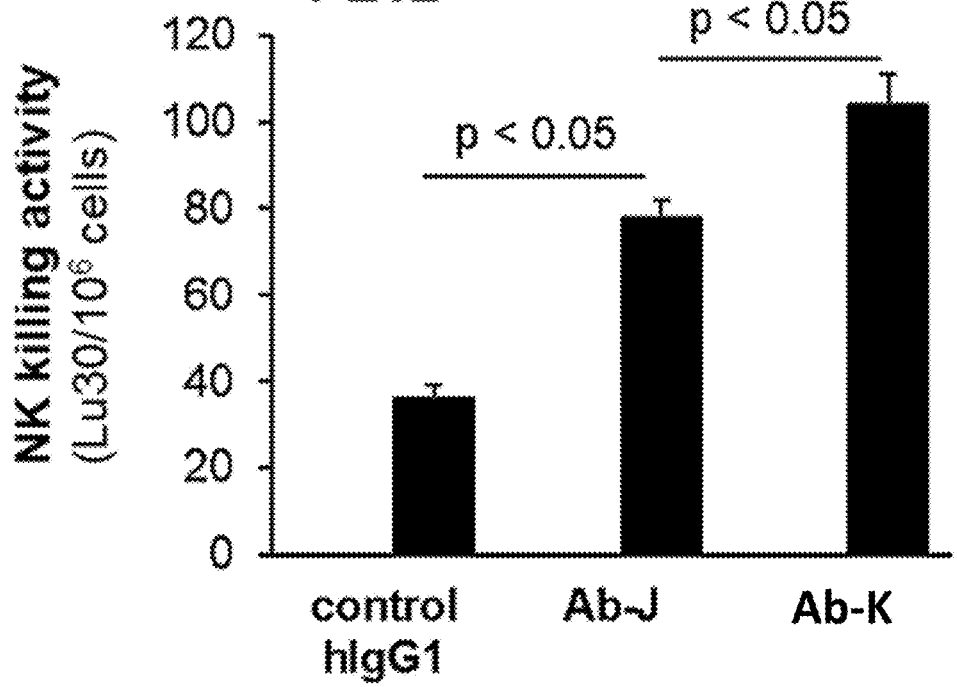

Referring to FIGS. 3A-3B, antibody K (Ab-K) demonstrates higher activity than chimeric antibody B10G5 in enhancing IL-2 activated primary NK cell killing of $MIC^+$ thyroid oncocytoma UC1 tumor cells (FIG. 3A); and pancreatic PL12 cells (also named Panc 10.05; FIG. 3B).

Example 6: Aggregation Assay

Samples of murine antibody B10G5, chimeric Ab-K antibody (ch-Ab-K, humanized variable region and murine Fc), and antibody K (Ab-K, humanized) were assayed using dynamic light scattering (DLS) with a quasi-elastic light scattering instrument. B10G5, ch-Ab-K, or Ab-K was respectively diluted in PBS buffer to the concentration of 1.0 mg/mL with a volume of 50 μL. All samples were filtered by spin-filtering (SpinX® Cat. #8160) to remove unwanted large particles and de-gassed before the assay. 5 μL samples were used to load respective disposable cuvette for DLS assay using the Unchained Lab nanoDLS pUNK machine. Details of the assay are described, for example, in Berne et al., Dynamic Light Scattering with Applications to Chemistry, Biology and Physics, Courier Dover Publications, ISBN 0-486-41155-9 (2000). In this assay, DLS measures fluctuations in scattered light intensity due to diffusing particles. The particles aggregate over time, seen as the increases in the hydrodynamic diameters (x-axis). Peak areas represent the respective levels of the different antibody species (e.g., the antibody monomers or aggregates), as a percentage of the total amount of the antibodies.

FIGS. 4A-4C respectively show the levels of the antibody monomers and aggregates for murine antibody B10G5 (a murine IgG1, FIG. 4A), chimeric Ab-K antibody (ch-Ab-K, composed of Ab-K humanized variable region with murine IgG1-Fc) (FIG. 4B), and Ab-K (humanized) (FIG. 4C). Both chimeric antibody ch-Ab-K and fully humanized antibody Ab-K are more stable in solution than murine antibody B10G5, as shown by the higher monomer levels of antibody chimeric Ab-K (FIG. 4B, 99.5%) and the fully humanized antibody Ab-K (FIG. 4C, 99.95%).

Example 7: Immunotherapy Clinical Trial

A Phase I clinical trial is conducted in cancer patients having MIC+ tumor samples or are serum sMIC+. The safety and maximum tolerable dose (MTD) and primary efficacy of MIC antibody are determined using an adaptive dose escalating 3+3 design or Time-to-Event Bayesian Optimal Interval design. The patient population includes those who failed standard care, but are chemo-naïve. The trial dose range of MIC antibody can be from 0.01 mg/Kg to 100 mg/Kg with I. V. infusion every 2-4 weeks for up to a 90-day period with up to 1 yr follow-up to determine MTD or recommended phase 2 dose (RP2D). For patients who do not present significant adverse effects, an extend period of infusion will be performed with up to 2 years of clinical follow-up to determine primary efficacy.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications, including patents, patent application publications, and scientific literature, are cited herein, the disclosures of which are incorporated by reference in their entireties for all purposes.

```
                        SEQUENCE LISTING

SEQ ID NO: 1 - VH amino acid sequence of HC2
EVQLQESGPG LVKPSQTLSL TCTVSGYSIT SDYAWNWIRQ PPGKGLEWIG YISYSGSTNY NPSLKSRVTI
SRDTSKNQFS LKLSSVTAAD TAVYYCARGG TYFDYWGQGT LVTVSS SEQ ID NO: 2 - VL amino acid sequence of LC3
DVVMTQSPST LSASVGDRVT ITCRASAHIN NWLAWYQQKP GKAPKLLISD ATSLESGVPS RFSGSGSGKE
YTLTISSLQP DDFATYYCQH YWSTPWTFGQ GTKVEIK SEQ ID NO: 3 - VH-IgG1 amino acid sequence
EVQLQESGPG LVKPSQTLSL TCTVSGYSIT SDYAWNWIRQ PPGKGLEWIG YISYSGSTNY NPSLKSRVTI
SRDTSKNQFS LKLSSVTAAD TAVYYCARGG TYFDYWGQGT LVTVSSASTK GPSVFPLAPS SKSTSGGTAA
LGCLVKDYFP EPVTVSWNSG ALTSGVHTFP AVLQSSGLYS LSSVVTVPSS SLGTQTYICN VNHKPSNTKV
DKKVEPKSCD KTHTCPPCPA PELLGGPSVF LFPPKPKDTL MISRTPEVTC VVVDVSHEDP EVKFNWYVDG
VEVHNAKTKP REEQYNSTYR VVSVLTVLHQ DWLNGKEYKC KVSNKALPAP IEKTISKAKG QPREPQVYTL
PPSRDELTKN QVSLTCLVKG FYPSDIAVEW ESNGQPENNY KTTPPVLDSD GSFFLYSKLT VDKSRWQQGN
VFSCSVMHEA LHNHYTQKSL SLSPG SEQ ID NO: 4 - VL-Igkappa amino acid sequence
DVVMTQSPST LSASVGDRVT ITCRASAHIN NWLAWYQQKP GKAPKLLISD ATSLESGVPS RFSGSGSGKE
YTLTISSLQP DDFATYYCQH YWSTPWTFGQ GTKVEIKRTV AAPSVFIFPP SDEQLKSGTA SVVCLLNNFY
PREAKVQWKV DNALQSGNSQ ESVTEQDSKD STYSLSSTLT LSKADYEKHK VYACEVTHQG LSSPVTKSFN
RGEC SEQ ID NO: 5 Signal Sequence
MDPKGSLSWR ILLFLSLAFE LSYG SEQ ID NO: 6 Signal Sequence
METDTLLLWV LLLWVPGSTG SEQ ID NO: 7 VH-IgG1 amino acid sequence with signal sequence
MDPKGSLSWR ILLFLSLAFE LSYGEVQLQE SGPGLVKPSQ TLSLTCTVSG YSITSDYAWN WIRQPPGKGL
EWIGYISYSG STNYNPSLKS RVTISRDTSK NQFSLKLSSV TAADTAVYYC ARGGTYFDYW GQGTLVTVSS
ASTKGPSVFP LAPSSKSTSG GTAALGCLVK DYFPEPVTVS WNSGALTSGV HTFPAVLQSS GLYSLSSVVT
VPSSSLGTQT YICNVNHKPS NTKVDKKVEP KSCDKTHTCP PCPAPELLGG PSVFLFPPKP KDTLMISRTP
EVTCVVVDVS HEDPEVKFNW YVDGVEVHNA KTKPREEQYN STYRVVSVLT VLHQDWLNGK EYKCKVSNKA
LPAPIEKTIS KAKGQPREPQ VYTLPPSRDE LTKNQVSLTC LVKGFYPSDI AVEWESNGQP ENNYKTTPPV
LDSDGSFFLY SKLTVDKSRW QQGNVFSCSV MHEALHNHYT QKSLSLSPG SEQ ID NO: 8 VL-Igkappa amino acid sequence with signal sequence
METDTLLLWV LLLWVPGSTG DVVMTQSPST LSASVGDRVT ITCRASAHIN NWLAWYQQKP GKAPKLLISD
ATSLESGVPS RFSGSGSGKE YTLTISSLQP DDFATYYCQH YWSTPWTFGQ GTKVEIKRTV AAPSVFIFPP
SDEQLKSGTA SVVCLLNNFY PREAKVQWKV DNALQSGNSQ ESVTEQDSKD STYSLSSTLT LSKADYEKHK
VYACEVTHQG LSSPVTKSFN RGEC SEQ ID NO: 9 Human MICA, isoform 1_
MGLGPVFLLL AGIFPFAPPG AAAEPHSLRY NLTVLSWDGS VQSGFLTEVH LDGQPFLRCD RQKCRAKPQG
QWAEDVLGNK TWDRETRDLT GNGKDLRMTL AHIKDQKEGL HSLQEIRVCE IHEDNSTRSS QHFYYDGELF
LSQNLETKEW TMPQSSRAQT LAMNVRNFLK EDAMKTKTHY HAMHADCLQE LRRYLKSGVV LRRTVPPMVN
VTRSEASEGN ITVTCRASGF YPWNITLSWR QDGVSLSHDT QQWGDVLPDG NGTYQTWVAT RICQGEEQRF
TCYMEHSGNH STHPVPSGKV LVLQSHWQTF HVSAVAAAAI FVIIIFYVRC CKKKTSAAEG PELVSLQVLD
QHPVGTSDHR DATQLGFQPL MSDLGSTGST EGA
```

SEQUENCE LISTING

SEQ ID NO: 10 Human MICB, isoform 1
MGLGRVLLFL AVAFPPAPPA AAAEPHSLRY NLMVLSQDGS VQSGFLAEGH LDGQPFLRYD RQKRRAKPQG
QWAENVLGAK TWDTETEDLT ENGQDLRRTL THIKDQKGGL HSLQEIRVCE IHEDSSTRGS RHFYYDGELF
LSQNLETQES TVPQSSRAQT LAMNVTNFWK EDAMKTKTHY RAMQADCLQK LQRYLKSGVA IRRTVPPMVN
VTCSEVSEGN ITVTCRASSF YPRNITLTWR QDGVSLSHNT QQWGDVLPDG NGTYQTWVAT RIRQGEEQRF
TCYMEHSGNH GTHPVPSGKA LVLQSQRTDF PYVSAAMPCF VIIIILCVPC CKKKTSAAEG PELVSLQVLD
QHPVGTGDHR DAAQLGFQPL MSATGSTGST EGT

SEQ ID NO: 11 VH CDR1
GYSITSDYA

SEQ ID NO: 12 VH CDR2
GYISYSGST

SEQ ID NO: 13 VH CDR3
ARGGTYFDY

SEQ ID NO: 14 VL CDRI
RASAHINNW

SEQ ID NO: 15 VL CDR2
DATSLES

SEQ ID NO: 16 VL CDR3
QHYWSTPWT

SEQ ID NO: 17
(Gly Gly Gly Gly Ser)n, where n = 1 to 5

SEQ ID NO: 18
His His His His His His

SEQ ID NO: 19 Coding Sequence for HC2
ATG GAC CCC AAG GGC AGC CTG AGC TGG AGA ATC CTG CTG TTC CTG AGC CTG GCC TTC
GAG CTG AGC TAC GGC GAA GTG CAG CTG CAG GAA TCT GGC CCT GGC CTC GTG AAG CCT
TCC CAG ACC CTG TCT CTG ACC TGC ACC GTG TCC GGC TAC TCC ATC ACC TCC GAC TAC
GCC TGG AAC TGG ATC CGG CAG CCT CCT GGC AAG CTG GAA TGG ATC GGC TAC ATC
TCC TAC TCC GGC TCC ACC AAC TAC AAC CCC AGC CTG AAG TCC AGA GTG ACC ATC TCC
CGG GAC ACC TCC AAG AAC CAG TTC TCC CTG AAG CTG TCC TCC GTG ACC GCC GCT GAT
ACC GCC GTG TAC TAC TGT GCT AGA GGC GGC ACC TAC TTC GAC TAC TGG GGC CAG GGC
ACC CTC GTG ACC GTG TCA TCT GCT AGC ACC AAG GGC CCC AGC GTG TTC CCT CTG GCC
CCC AGC AGC AAG AGC ACC AGC GGC GGA ACC GCC GCC CTG GGC TGC CTG GTG AAG GAC
TAC TTC CCC GAG CCC GTG ACC GTG TCC TGG AAC AGC GGC GCT CTG ACC AGC GGA GTG
CAC ACC TTC CCT GCC GTG CTG CAG AGC AGC GGC CTG TAC TCC CTG AGC AGC GTG GTG
ACC GTG CCC AGC AGC AGC CTG GGC ACC CAG ACC TAC ATC TGC AAC GTG AAC CAC AAG
CCC TCC AAC ACC AAG GTG GAC AAG AAG GTG GAG CCT AAG AGC TGC GAC AAG ACC CAC
ACC TGC CCT CCC TGC CCC GCC CCC GAG CTG CTG GGC GGA CCC AGC GTG TTC CTG TTC
CCT CCC AAG CCC AAG GAC ACC CTG ATG ATC AGC CGG ACC CCC GAG GTG ACC TGC GTG
GTG GTG GAC GTG AGC CAC GAG GAC CCC GAG GTG AAG TTC AAC TGG TAC GTG GAC GGC
GTG GAG GTG CAC AAC GCC AAG ACC AAG CCT CGG GAG GAG CAG TAC AAC TCC ACC TAC
CGC GTG GTG AGC GTG CTG ACC GTG CTG CAC CAG GAC TGG CTG AAC GGC AAG GAG TAC
AAG TGC AAG GTG AGC AAC AAG GCC CTG CCC GCT CCC ATC GAG AAG ACC ATC AGC AAG
GCC AAG GGC CAG CCC CGG GAG CCT CAG GTG TAC ACC CTG CCC CCT AGC CGC GAC GAG
CTG ACC AAG AAC CAG GTG AGC CTG ACC TGC CTG GTG AAG GGC TTC TAC CCC TCC GAC
ATC GCC GTG GAG TGG GAG AGC AAC GGC CAG CCT GAG AAC AAC TAC AAG ACC ACC CCT
CCC GTG CTG GAC AGC GAC GGC AGC TTC TTC CTG TAC AGC AAG CTG ACC GTG GAC AAG
TCC CGG TGG CAG CAG GGC AAC GTG TTC AGC TGC AGC GTG ATG CAC GAG GCC CTG CAC
AAC CAC TAC ACC CAG AAG AGC CTG AGC CTG AGC CCC GGA TAG TAA SEQ ID NO: 20 Coding Sequence for LC3
ATG GAG ACC GAC ACC CTG CTG CTC TGG GTG CTG CTG CTC TGG GTG CCC GGC TCC ACC
GGA GAC GTC GTG ATG ACC CAG TCC CCC TCC ACA CTG TCT GCC TCT GTG GGC GAC AGA
GTG ACC ATC ACC TGT CGG GCC TCC GCC CAC ATC AAC AAC TGG CTG GCC TGG TAT CAG
CAG AAG CCC GGC AAG GCC CCT AAG CTG CTG ATC TCT GAT GCC ACC TCC CTG GAA TCC
GGC GTG CCC TCC AGA TTC TCC GGC TCT GGC TCT GGC AAG GAG TAT ACC CTG ACC ATC
AGC TCC CTG CAG CCC GAT GAC TTC GCC ACC TAC TAC TGC CAG CAC TAC TGG TCC ACC
CCC TGG ACC TTT GGC CAA GGC ACC AAG GTG GAA ATC AAG CGG ACC GTG GCC GCC CCC
AGC GTG TTC ATC TTC CCT CCC AGC GAC GAG CAG CTG AAG TCT GGC ACC GCC AGC GTG
GTG TGC CTG CTG AAC AAC TTC TAC CCC CGC GAG GCC AAG GTG CAG TGG AAG GTG GAC
AAC GCC CTG CAG AGC GGC AAC AGC CAG GAG AGC GTG ACC GAG CAG GAC TCC AAG GAC
AGC ACC TAC AGC CTG AGC AGC ACC CTG ACC CTG AGC AAG GCC GAC TAC GAG AAG CAC
AAG GTG TAC GCC TGC GAG GTG ACC CAC CAG GGA CTG TCT AGC CCC GTG ACC AAG AGC
TTC AAC CGG GGC GAG TGC TAA

SEQUENCE LISTING

```
SEQ ID NO: 21 VH Coding Region
GAA GTG CAG CTG CAG GAA TCT GGC CCT GGC CTC GTG AAG CCT TCC CAG ACC CTG TCT
CTG ACC TGC ACC GTG TCC GGC TAC TCC ATC ACC GAC TAC GCC TGG AAC TGG ATC
CGG CAG CCT CCT GGC AAG GGA CTG GAA TGG ATC GGC TAC ATC TCC TAC TCC GGC TCC
ACC AAC TAC AAC CCC AGC CTG AAG TCC AGA GTG ACC ATC TCC CGG GAC ACC TCC AAG
AAC CAG TTC TCC CTG AAG CTG TCC TCC GTG ACC GCC GCT GAT ACC GCC GTG TAC TAC
TGT GCT AGA GGC GGC ACC TAC TTC GAC TAC TGG GGC CAG GGC ACC CTC GTG ACC GTG
TCA TCT SEQ ID NO: 22 VL Coding Region
GAC GTC GTG ATG ACC CAG TCC CCC TCC ACA CTG TCT GCC TCT GTG GGC GAC AGA GTG
ACC ATC ACC TGT CGG GCC TCC GCC CAC ATC AAC AAC TGG CTG GCC TGG TAT CAG CAG
AAG CCC GGC AAG GCC CCT AAG CTG CTG ATC TCT GAT GCC ACC TCC CTG GAA TCC GGC
GTG CCC TCC AGA TTC TCC GGC TCT GGC TCT GGC AAG GAG TAT ACC CTG ACC ATC AGC
TCC CTG CAG CCC GAT GAC TTC GCC ACC TAC TAC TGC CAG CAC TAC TGG TCC ACC CCC
TGG ACC TTT GGC CAA GGC ACC AAG GTG GAA ATC AAG SEQ ID NO: 23 VH amino acid sequence of HC1
QVQLQESGPG LVKPSQTLSL TCTVSGYSIT SDYAWNWIRQ PPGKGLEWIG YISYSGSTNY NPSLKSRVTI
SVDTSKNQFS LKLSSVTAAD TAVYYCARGG TYFDYWGQGT LVTVSS SEQ ID NO: 24 VH amino acid sequence of HC3
EVQLVESGPG LVKPSETLSL TCTVSGYSIT SDYAWNWIRQ PPGKGLEWIG YISYSGSTNY NPSLKSRVTI
SRDTSKNQFS LKLSSVTAAD TAVYYCARGG TYFDYWGQGT TVTVSS SEQ ID NO: 25 VL amino acid sequence of LC1
DIQMTQSPSS LSASVGDRVT ITCRASAHIN NWLAWYQQKP GKAPKLLLSD ATSLESGVPS RFSGSGSGTD
YTLTISSLQP EDFATYYCQH YWSTPWTFGG GTKVEIK SEQ ID NO: 26 VL amino acid sequence of LC2
DIVMTQSPSS LSASVGDRVT ITCRASAHIN NWLAWYQQKP GKAPKLLLSD ATSLESGVPS RFSGSGSGKD
YTLTISSLQP EDFATYYCQH YWSTPWTFGG GTKVEIK SEQ ID NO: 27 Soluble MICA
EPHSLRYNLT VLSWDGSVQS GFLAEVHLDG QPFLRCDRQK CRAKPQGQWA EDVLGNKTWD RETRDLTGNG
KDLRMTLAHI KDQKEGLHSL QEIRVCEIHE DNSTRSSQHF YYDGELFLSQ NLETEEWTMP QSSRAQTLAM
NIRNFLKEDA MKTKTHYHAM HADCLQELRR YLKSGVVLRR TVPPMVNVTR SEASEGNITV TCRASGFYPW
NITLSWRQDG VSLSHDTQQW GDVLPDGNGT YQTWVATRIC QGEEQRFTCY MEHSGNHSTH PVPS SEQ ID NO:28 Soluble MICB
EPHSLRYNLM VLSQDGSVQS GFLAEGHLDG QPFLRYDRQK RRAKPQGQWA EDVLGAKTWD TETEDLTENG
QDLRRTLTHI KDQKGGLHSL QEIRVCEIHE DSSTRGSRHF YYDGELFLSQ NLETQESTVP QSSRAQTLAM
NVTNFWKEDA MKTKTHYRAM QADCLQKLQR YLKSGVAIRR TVPPMVNVTC SEVSEGNITV TCRASSFYPR
NITLTWRQDG VSLSHNTQQW GDVLPDGNGT YQTWVATRIR QGEEQRFTCY MEHSGNHGTH PVPS SEQ ID NO: 29 IGHV4-59*11 (MK471385)
QVQLQESGPG LVKPSETLSL TCTVSGGSIS SHYWSWIRQP PGKGLEWIGY IYYSGSTNYN PSLKSRVTIS
VDTSKNQFSL KLSSVTAADT AVYYCAR

SEQ ID NO: 30 IGHJ4*01
YFDYWGQGTL VTVSS

SEQ ID NO: 31 IGHV4-30-4*01 (Z14238)
QVQLQESGPG LVKPSQTLSL TCTVSGGSIS SGDYYWSWIR QPPGKGLEWI GYIYYSGSTYY NPSLKSRVTI
VDTSKNQFSL KLSSVTAADT AVYYCAR

SEQ ID NO: 32 IGKV1-NL1-4*01 (Y14865)
DIQMTQSPSS LSASVGDRVT ITCRASQGIS NSLAWYQQKP GKAPKLLLYA ASRLESGVPS RFSGSGSGTD
YTLTISSLQP EDFATYYCQQ YYSTP

SEQ ID NO: 33 IGKJ1*01 (J00242)
WTFGQGTKVE IK

SEQ ID NO: 34 IGKV1-33*01 (M64856)
DIQMTQSPSS LSASVGDRVT ITCQASQDIS NYLNWYQQKP GKAPKLLIYD ASNLETGVPS RFSGSGSGTD
FTFTISSLQP EDIATYYCQQ YDNLP

SEQ ID NO: 35 IGKV1-5*01 (Z00001)
DIQMTQSPST LSASVGDRVT ITCRASQSIS SWLAWYQQKP GKAPKLLIYD ASSLESGVPS RFSGSGSGTE
FTLTISSLQP DDFATYYCQQ YNSYS

SEQ ID NO: 36 B10G5 VH
EVQLEESGPG LVKPSQSLSL TCTVTGYSIT SDYAWNWIRQ FPGNKLEWMG YISYSGSTNY NPSLKSRISI
TRDTSKNQFF LQLNSVITED TATYYCARGG TYFDYWGQGT TLTVSS
```

-continued

SEQUENCE LISTING

SEQ ID NO: 37 B10G5 VL
DIVLTQTTSY LSVSLGGRVT IACKASAHIN NWLAWYQQKP GNAPRLLISD ATSLETGVPS RFSGSGSGKD
YTLSITSLQT EDVATYYCQH YWSTPWTFGG GTKLEIK

SEQ ID NO: 38 Flexible Sequence
GGGS

---

SEQUENCE LISTING

```
Sequence total quantity: 38
SEQ ID NO: 1              moltype = AA   length = 116
FEATURE                   Location/Qualifiers
REGION                    1..116
                          note = VH amino acid sequence of HC2
source                    1..116
                          mol_type = protein
                          organism = synthetic construct
SEQUENCE: 1
EVQLQESGPG LVKPSQTLSL TCTVSGYSIT SDYAWNWIRQ PPGKGLEWIG YISYSGSTNY    60
NPSLKSRVTI SRDTSKNQFS LKLSSVTAAD TAVYYCARGG TYFDYWGQGT LVTVSS        116

SEQ ID NO: 2              moltype = AA   length = 107
FEATURE                   Location/Qualifiers
REGION                    1..107
                          note = VL amino acid sequence of LC3
source                    1..107
                          mol_type = protein
                          organism = synthetic construct
SEQUENCE: 2
DVVMTQSPST LSASVGDRVT ITCRASAHIN NWLAWYQQKP GKAPKLLISD ATSLESGVPS    60
RFSGSGSGKE YTLTISSLQP DDFATYYCQH YWSTPWTFGQ GTKVEIK                  107

SEQ ID NO: 3              moltype = AA   length = 445
FEATURE                   Location/Qualifiers
REGION                    1..445
                          note = VH-IgG1 amino acid sequence
source                    1..445
                          mol_type = protein
                          organism = synthetic construct
SEQUENCE: 3
EVQLQESGPG LVKPSQTLSL TCTVSGYSIT SDYAWNWIRQ PPGKGLEWIG YISYSGSTNY    60
NPSLKSRVTI SRDTSKNQFS LKLSSVTAAD TAVYYCARGG TYFDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 4              moltype = AA   length = 214
FEATURE                   Location/Qualifiers
REGION                    1..214
                          note = VL-Igkappa amino acid sequence
source                    1..214
                          mol_type = protein
                          organism = synthetic construct
SEQUENCE: 4
DVVMTQSPST LSASVGDRVT ITCRASAHIN NWLAWYQQKP GKAPKLLISD ATSLESGVPS    60
RFSGSGSGKE YTLTISSLQP DDFATYYCQH YWSTPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 5              moltype = AA   length = 24
FEATURE                   Location/Qualifiers
REGION                    1..24
                          note = Signal Sequence
source                    1..24
                          mol_type = protein
                          organism = synthetic construct
SEQUENCE: 5
MDPKGSLSWR ILLFLSLAFE LSYG                                           24

SEQ ID NO: 6              moltype = AA   length = 20
```

```
FEATURE                 Location/Qualifiers
REGION                  1..20
                        note = Signal Sequence
source                  1..20
                        mol_type = protein
                        organism = synthetic construct
SEQUENCE: 6
METDTLLLWV LLLWVPGSTG                                                    20

SEQ ID NO: 7            moltype = AA  length = 469
FEATURE                 Location/Qualifiers
REGION                  1..469
                        note = VH-IgG1 amino acid sequence with signal sequence
source                  1..469
                        mol_type = protein
                        organism = synthetic construct
SEQUENCE: 7
MDPKGSLSWR ILLFLSLAFE LSYGEVQLQE SGPGLVKPSQ TLSLTCTVSG YSITSDYAWN   60
WIRQPPGKGL EWIGYISYSG STNYNPSLKS RVTISRDTSK NQFSLKLSSV TAADTAVYYC  120
ARGGTYFDYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSRDE LTKNQVSLTC LVKGFYPSDI AVEWESNGQP ENNYKTTPPV  420
LDSDGSFFLY SKLTVDKSRW QQGNVFSCSV MHEALHNHYT QKSLSLSPG              469

SEQ ID NO: 8            moltype = AA  length = 234
FEATURE                 Location/Qualifiers
REGION                  1..234
                        note = VL-Igkappa amino acid sequence with signal sequence
source                  1..234
                        mol_type = protein
                        organism = synthetic construct
SEQUENCE: 8
METDTLLLWV LLLWVPGSTG DVVMTQSPST LSASVGDRVT ITCRASAHIN NWLAWYQQKP   60
GKAPKLLISD ATSLESGVPS RFSGSGSGKE YTLTISSLQP DDFATYYCQH YWSTPWTFGQ  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 9            moltype = AA  length = 383
FEATURE                 Location/Qualifiers
source                  1..383
                        mol_type = protein
                        organism = Homo sapiens
SEQUENCE: 9
MGLGPVFLLL AGIFPFAPPG AAAEPHSLRY NLTVLSWDGS VQSGFLTEVH LDGQPFLRCD   60
RQKCRAKPQG QWAEDVLGNK TWDRETRDLT GNGKDLRMTL AHIKDQKEGL HSLQEIRVCE  120
IHEDNSTRSS QHFYYDGELF LSQNLETKEW TMPQSSRAQT LAMNVRNFLK EDAMKTKTHY  180
HAMHADCLQE LRRYLKSGVV LRRTVPPMVN VTRSEASEGN ITVTCRASGF YPWNITLSWR  240
QDGVSLSHDT QQWGDVLPDG NGTYQTWVAT RICQGEEQRF TCYMEHSGNH STHPVPSGKV  300
LVLQSHWQTF HVSAVAAAAI FVIIIFYVRC CKKKTSAAEG PELVSLQVLD QHPVGTSDHR  360
DATQLGFQPL MSDLGSTGST EGA                                          383

SEQ ID NO: 10           moltype = AA  length = 383
FEATURE                 Location/Qualifiers
source                  1..383
                        mol_type = protein
                        organism = Homo sapiens
SEQUENCE: 10
MGLGRVLLFL AVAFPFAPPA AAAEPHSLRY NLMVLSQDGS VQSGFLAEGH LDGQPFLRYD   60
RQKRRAKPQG QWAENVLGAK TWDTETEDLT ENGQDLRRTL THIKDQKGGL HSLQEIRVCE  120
IHEDSSTRGS RHFYYDGELF LSQNLETQES TVPQSSRAQT LAMNVTNFWK EDAMKTKTHY  180
RAMQADCLQK LQRYLKSGVA IRRTVPPMVN VTCSEVSEGN ITVTCRASSF YPRNITLTWR  240
QDGVSLSHNT QQWGDVLPDG NGTYQTWVAT RIRQGEEQRF TCYMEHSGNH GTHPVPSGKA  300
LVLQSQRTDF PYVSAAMPCF VIIIILCVPC CKKKTSAAEG PELVSLQVLD QHPVGTGDHR  360
DAAQLGFQPL MSATGSTGST EGT                                          383

SEQ ID NO: 11           moltype = AA  length = 9
FEATURE                 Location/Qualifiers
REGION                  1..9
                        note = VH CDR1
source                  1..9
                        mol_type = protein
                        organism = synthetic construct
SEQUENCE: 11
GYSITSDYA                                                            9

SEQ ID NO: 12           moltype = AA  length = 9
FEATURE                 Location/Qualifiers
```

```
REGION                  1..9
                        note = VH CDR2
source                  1..9
                        mol_type = protein
                        organism = synthetic construct
SEQUENCE: 12
GYISYSGST                                                                 9

SEQ ID NO: 13           moltype = AA  length = 9
FEATURE                 Location/Qualifiers
REGION                  1..9
                        note = VH CDR3
source                  1..9
                        mol_type = protein
                        organism = synthetic construct
SEQUENCE: 13
ARGGTYFDY                                                                 9

SEQ ID NO: 14           moltype = AA  length = 9
FEATURE                 Location/Qualifiers
REGION                  1..9
                        note = VL CDR1
source                  1..9
                        mol_type = protein
                        organism = synthetic construct
SEQUENCE: 14
RASAHINNW                                                                 9

SEQ ID NO: 15           moltype = AA  length = 7
FEATURE                 Location/Qualifiers
REGION                  1..7
                        note = VL CDR2
source                  1..7
                        mol_type = protein
                        organism = synthetic construct
SEQUENCE: 15
DATSLES                                                                   7

SEQ ID NO: 16           moltype = AA  length = 9
FEATURE                 Location/Qualifiers
REGION                  1..9
                        note = VL CDR3
source                  1..9
                        mol_type = protein
                        organism = synthetic construct
SEQUENCE: 16
QHYWSTPWT                                                                 9

SEQ ID NO: 17           moltype = AA  length = 25
FEATURE                 Location/Qualifiers
REGION                  1..25
                        note = Synthetic linker
REGION                  6..25
                        note = MISC_FEATURE - (G4S)n linker where n = 1 to 5
source                  1..25
                        mol_type = protein
                        organism = synthetic construct
SEQUENCE: 17
GGGGSGGGGS GGGGSGGGGS GGGGS                                              25

SEQ ID NO: 18           moltype = AA  length = 6
FEATURE                 Location/Qualifiers
REGION                  1..6
                        note = Hexahistidinyl tag
source                  1..6
                        mol_type = protein
                        organism = synthetic construct
SEQUENCE: 18
HHHHHH                                                                    6

SEQ ID NO: 19           moltype = DNA  length = 1413
FEATURE                 Location/Qualifiers
misc_feature            1..1413
                        note = Coding Sequence for HC2
source                  1..1413
                        mol_type = other DNA
                        organism = synthetic construct
SEQUENCE: 19
atggacccca agggcagcct gagctggaga atcctgctgt tcctgagcct ggccttcgag       60
```

```
                                                           -continued ctgagctacg gcgaagtgca gctgcaggaa tctggccctg gcctcgtgaa gccttcccag    120
accctgtctc tgacctgcac cgtgtccggc tactccatca cctccgacta cgcctggaac    180
tggatccggc agcctcctgg caagggactg aatggatcgg ctacatctc ctactccggc    240
tccaccaact acaaccccag cctgaagtcc agagtgacca tctcccggga cacctccaag    300
aaccagttct ccctgaagct gtcctccgtg accgccgtg ataccgccgt gtactactgt    360
gctagaggcg gcacctactt cgactactgg ggccagggca cctcgtgac cgtgtcatct    420
gctagcacca agggccccag cgtgttccct ctggccccca gcagcaagag caccagcggc    480
ggaaccgccg ccctgggctg cctggtgaag gactacttcc ccgagccgt gaccgtgtcc    540
tggaacagcg gcgctctgac cagcggagtg cacaccttcc ctgccgtgct gcagagcagc    600
ggcctgtact ccctgagcag cgtggtgacc gtgcccagca gcagcctggg cacccagacc    660
tacatctgca acgtgaacca caagccctcc aacaccaagg tggacaagaa ggtgagcct    720
aagagctgcg acaagaccca cacctgccct cctgccccg ccccgagct gctgggcgga    780
cccagcgtgt tcctgttccc tcccaagccc aaggacaccc tgatgatcag ccgcaccccc    840
gaggtgacct gcgtggtggt ggacgtgagc cacgaggacc ccgaggtgaa gttcaactgg    900
tacgtggacg gcgtggaggt gcacaacgcc aagaccaagc ctcgggagga gcagtacaac    960
tccacctacc gcgtggtgag cgtgctgacc gtgctgcacc aggactggct gaacggcaag   1020
gagtacaagt gcaaggtgag caacaaggcc ctgcccgctc ccatcgagaa gaccatcagc   1080
aaggccaagg gccagccccg ggagcctcag cgtgtacacc tgcccccag ccgcgacgag   1140
ctgaccaaga accaggtgag cctgacctgc ctggtgaagg gcttctaccc ctccgacatc   1200
gccgtggagt gggagagcaa cggccagcct gagaacaact acaagaccac ccctcccgtg   1260
ctggacagcg acggcagctt cttcctgtac agcaagctga ccgtggacaa gtcccggtgg   1320
cagcagggca acgtgttcag ctgcagcgtg atgcacgagg ccctgcacaa ccactacacc   1380
cagaagagcc tgagcctgag ccccggatag taa                                1413

SEQ ID NO: 20         moltype = DNA  length = 705
FEATURE               Location/Qualifiers
misc_feature          1..705
                      note = Coding Sequence for LC3
source                1..705
                      mol_type = other DNA
                      organism = synthetic construct
SEQUENCE: 20
atggagaccg acaccctgct gctctgggtg ctgctgctct gggtgccgg ctccaccgga     60
gacgtcgtga tgacccagtc ccctccaca ctgtctgcct ctgtgggcga cagagtgacc    120
atcacctgtc gggcctccgc ccacatcaac aactggctgg cctggtatca gcagaagccc    180
ggcaaggccc ctaagctgct gatctctgat gccacctccc tggaatcgg cgtgccctcc    240
agattctccg gctctggctc tggcaaggag tataccctga ccatcagctc cctgcagccc    300
gatgacttcg ccacctacta ctgccagcac tactggtcca ccctggac ctttggccaa     360
ggcaccaagg tggaaatcaa gcggaccgtg gccgccccca gcgtgttcat cttccctcca    420
agcgacgagc agctgaagtc tggcaccgcc agcgtggtgt gcctgctgaa caacttctac    480
ccccgcgagg ccaaggtgca gtggaaggtg gacaacgccc tgcagagcgg caacagccag    540
gagagcgtga ccgagcagga ctccaaggac agcacctaca gcctgagcag cacccctgacc    600
ctgagcaagg ccgactacga aagcacaag gtgtacgcct gcgaggtgac ccaccaggga    660
ctgtctagcc ccgtgaccaa gagcttcaac cggggcgagt gctaa                   705

SEQ ID NO: 21         moltype = DNA  length = 348
FEATURE               Location/Qualifiers
misc_feature          1..348
                      note = VH Coding Region
source                1..348
                      mol_type = other DNA
                      organism = synthetic construct
SEQUENCE: 21
gaagtgcagc tgcaggaatc tggccctggc ctcgtgaagc cttcccagac cctgtctctg     60
acctgcaccg tgtccggcta ctccatcacc tccgactacg cctggaactg gatccggcag    120
cctcctggca agggactgga atggatcggc tacatctcct actccggctc caccaactac    180
aaccccagcc tgaagtccag agtgaccatc tcccgggaca cctccaagaa ccagttctcc    240
ctgaagctgt cctccgtgac cgccgctgat accgccgtgt actactgtgc tagaggcggc    300
acctacttcg actactgggg ccagggcacc ctcgtgaccg tgtcatct                 348

SEQ ID NO: 22         moltype = DNA  length = 321
FEATURE               Location/Qualifiers
misc_feature          1..321
                      note = VL Coding Region
source                1..321
                      mol_type = other DNA
                      organism = synthetic construct
SEQUENCE: 22
gacgtcgtga tgacccagtc ccctccaca ctgtctgcct ctgtgggcga cagagtgacc      60
atcacctgtc gggcctccgc ccacatcaac aactggctgg cctggtatca gcagaagccc    120
ggcaaggccc ctaagctgct gatctctgat gccacctccc tggaatcgg cgtgccctcc    180
agattctccg gctctggctc tggcaaggag tataccctga ccatcagctc cctgcagccc    240
gatgacttcg ccacctacta ctgccagcac tactggtcca ccctggac ctttggccaa     300
ggcaccaagg tggaaatcaa g                                              321

SEQ ID NO: 23         moltype = AA   length = 116
FEATURE               Location/Qualifiers
REGION                1..116
                      note = VH amino acid sequence of HC1
```

```
                        source          1..116
                                        mol_type = protein
                                        organism = synthetic construct
SEQUENCE: 23
QVQLQESGPG LVKPSQTLSL TCTVSGYSIT SDYAWNWIRQ PPGKGLEWIG YISYSGSTNY      60
NPSLKSRVTI SVDTSKNQFS LKLSSVTAAD TAVYYCARGG TYFDYWGQGT LVTVSS         116

SEQ ID NO: 24           moltype = AA  length = 116
FEATURE                 Location/Qualifiers
REGION                  1..116
                        note = VH amino acid sequence of HC3
source                  1..116
                        mol_type = protein
                        organism = synthetic construct
SEQUENCE: 24
EVQLVESGPG LVKPSETLSL TCTVSGYSIT SDYAWNWIRQ PPGKGLEWIG YISYSGSTNY      60
NPSLKSRVTI SRDTSKNQFS LKLSSVTAAD TAVYYCARGG TYFDYWGQGT TVTVSS         116

SEQ ID NO: 25           moltype = AA  length = 107
FEATURE                 Location/Qualifiers
REGION                  1..107
                        note = VL amino acid sequence of LC1
source                  1..107
                        mol_type = protein
                        organism = synthetic construct
SEQUENCE: 25
DIQMTQSPSS LSASVGDRVT ITCRASAHIN NWLAWYQQKP GKAPKLLLSD ATSLESGVPS      60
RFSGSGSGTD YTLTISSLQP EDFATYYCQH YWSTPWTFGG GTKVEIK                  107

SEQ ID NO: 26           moltype = AA  length = 107
FEATURE                 Location/Qualifiers
REGION                  1..107
                        note = VL amino acid sequence of LC2
source                  1..107
                        mol_type = protein
                        organism = synthetic construct
SEQUENCE: 26
DIVMTQSPSS LSASVGDRVT ITCRASAHIN NWLAWYQQKP GKAPKLLLSD ATSLESGVPS      60
RFSGSGSGKD YTLTISSLQP EDFATYYCQH YWSTPWTFGG GTKVEIK                  107

SEQ ID NO: 27           moltype = AA  length = 274
FEATURE                 Location/Qualifiers
source                  1..274
                        mol_type = protein
                        organism = Homo sapiens
SEQUENCE: 27
EPHSLRYNLT VLSWDGSVQS GFLAEVHLDG QPFLRCDRQK CRAKPQGQWA EDVLGNKTWD      60
RETRDLTGNG KDLRMTLAHI KDQKEGLHSL QEIRVCEIHE DNSTRSSQHF YYDGELFLSQ     120
NLETEEWTMP QSSRAQTLAM NIRNFLKEDA MKTKTHYHAM HADCLQELRR YLKSGVVLRR     180
TVPPMVNVTR SEASEGNITV TCRASGFYPW NITLSWRQDG VSLSHDTQQW GDVLPDGNGT     240
YQTWVATRIC QGEEQRFTCY MEHSGNHSTH PVPS                                274

SEQ ID NO: 28           moltype = AA  length = 274
FEATURE                 Location/Qualifiers
source                  1..274
                        mol_type = protein
                        organism = Homo sapiens
SEQUENCE: 28
EPHSLRYNLM VLSQDGSVQS GFLAEGHLDG QPFLRYDRQK RRAKPQGQWA EDVLGAKTWD      60
TETEDLTENG QDLRRTLTHI KDQKGGLHSL QEIRVCEIHE DSSTRGSRHF YYDGELFLSQ     120
NLETQESTVP QSSRAQTLAM NVTNFWKEDA MKTKTHYRAM QADCLQKLQR YLKSGVAIRR     180
TVPPMVNVTC SEVSEGNITV TCRASSFYPR NITLTWRQDG VSLSHNTQQW GDVLPDGNGT     240
YQTWVATRIR QGEEQRFTCY MEHSGNHGTH PVPS                                274

SEQ ID NO: 29           moltype = AA  length = 97
FEATURE                 Location/Qualifiers
source                  1..97
                        mol_type = protein
                        organism = Homo sapiens
SEQUENCE: 29
QVQLQESGPG LVKPSETLSL TCTVSGGSIS SHYWSWIRQP PGKGLEWIGY IYYSGSTNYN      60
PSLKSRVTIS VDTSKNQFSL KLSSVTAADT AVYYCAR                              97

SEQ ID NO: 30           moltype = AA  length = 15
FEATURE                 Location/Qualifiers
source                  1..15
                        mol_type = protein
                        organism = Homo sapiens
SEQUENCE: 30
```

```
YFDYWGQGTL VTVSS                                                           15

SEQ ID NO: 31           moltype = AA   length = 98
FEATURE                 Location/Qualifiers
source                  1..98
                        mol_type = protein
                        organism = Homo sapiens
SEQUENCE: 31
QVQLQESGPG LVKPSQTLSL TCTVSGGSIS SGDYYWSWIR QPPGKGLEWI GYIYYSGSTY           60
YNPSLKSRVT IVDTSKNQFS LKLSSVTAAD TAVYYCAR                                  98

SEQ ID NO: 32           moltype = AA   length = 95
FEATURE                 Location/Qualifiers
source                  1..95
                        mol_type = protein
                        organism = Homo sapiens
SEQUENCE: 32
DIQMTQSPSS LSASVGDRVT ITCRASQGIS NSLAWYQQKP GKAPKLLLYA ASRLESGVPS           60
RFSGSGSGTD YTLTISSLQP EDFATYYCQQ YYSTP                                     95

SEQ ID NO: 33           moltype = AA   length = 12
FEATURE                 Location/Qualifiers
source                  1..12
                        mol_type = protein
                        organism = Homo sapiens
SEQUENCE: 33
WTFGQGTKVE IK                                                              12

SEQ ID NO: 34           moltype = AA   length = 95
FEATURE                 Location/Qualifiers
source                  1..95
                        mol_type = protein
                        organism = Homo sapiens
SEQUENCE: 34
DIQMTQSPSS LSASVGDRVT ITCQASQDIS NYLNWYQQKP GKAPKLLIYD ASNLETGVPS           60
RFSGSGSGTD FTFTISSLQP EDIATYYCQQ YDNLP                                     95

SEQ ID NO: 35           moltype = AA   length = 95
FEATURE                 Location/Qualifiers
source                  1..95
                        mol_type = protein
                        organism = Homo sapiens
SEQUENCE: 35
DIQMTQSPST LSASVGDRVT ITCRASQSIS SWLAWYQQKP GKAPKLLIYD ASSLESGVPS           60
RFSGSGSGTE FTLTISSLQP DDFATYYCQQ YNSYS                                     95

SEQ ID NO: 36           moltype = AA   length = 116
FEATURE                 Location/Qualifiers
REGION                  1..116
                        note = B10G5 VH
source                  1..116
                        mol_type = protein
                        organism = synthetic construct
SEQUENCE: 36
EVQLEESGPG LVKPSQSLSL TCTVTGYSIT SDYAWNWIRQ FPGNKLEWMG YISYSGSTNY           60
NPSLKSRISI TRDTSKNQFF LQLNSVITED TATYYCARGG TYFDYWGQGT TLTVSS              116

SEQ ID NO: 37           moltype = AA   length = 107
FEATURE                 Location/Qualifiers
REGION                  1..107
                        note = B10G5 VL
source                  1..107
                        mol_type = protein
                        organism = synthetic construct
SEQUENCE: 37
DIVLTQTTSY LSVSLGGRVT IACKASAHIN NWLAWYQQKP GNAPRLLISD ATSLETGVPS           60
RFSGSGSGKD YTLSITSLQT EDVATYYCQH YWSTPWTFGG GTKLEIK                        107

SEQ ID NO: 38           moltype = AA   length = 4
FEATURE                 Location/Qualifiers
source                  1..4
                        mol_type = protein
                        organism = synthetic construct
SEQUENCE: 38
GGGS                                                                        4
```

The invention claimed is:

1. An isolated monoclonal antibody or antigen-binding portion thereof that specifically binds MIC, wherein the antibody or antigen-binding portion thereof each comprises a heavy chain variable (VH) region and a light chain variable (VL) region, wherein the VH region comprises a complementarity determining region HCDR1 sequence having the amino acid sequence set forth in SEQ ID NO:11, a HCDR2 having the amino acid sequence set forth in SEQ ID NO:12, and a HCDR3 having the amino acid sequence set forth in SEQ ID NO:13, and wherein the VL region comprises a LCDR1 sequence having the amino acid sequence set forth in SEQ ID NO:14, a LCDR2 having the amino acid sequence set forth in SEQ ID NO:15, and a LCDR3 having the amino acid sequence set forth in SEQ ID NO:16, wherein the VH region comprises an amino acid sequence that is at least 90% identical to the amino acid sequence of SEQ ID NO: 1, and the VL region comprises an amino acid sequence that is at least 90% identical to the amino acid sequence of SEQ ID NO: 2.

2. The isolated antibody or antigen-binding portion thereof of claim 1, wherein the VH region comprises an amino acid sequence that is at least 95% identical to the amino acid sequence of SEQ ID NO: 1.

3. The isolated antibody or antigen-binding portion thereof of claim 1, wherein the VH region comprises the amino acid sequence of SEQ ID NO: 1.

4. The isolated antibody or antigen-binding portion thereof of claim 1, wherein the VL region comprises the amino acid sequence of SEQ ID NO: 2.

5. The isolated antibody or antigen-binding portion thereof of claim 1, wherein the VH region comprises the amino acid sequence of SEQ ID NO: 1 and the VL region comprises the amino acid sequence of SEQ ID NO: 2.

6. The isolated antibody or antigen binding fragment thereof of claim 1, which is an antigen-binding fragment selected from a Fab, a Fab', an F(ab')$_2$, an Fv, a disulfide linked Fv, and a scFv.

7. The isolated antibody or antigen-binding fragment thereof of claim 5, wherein the antibody comprises a heavy chain comprising the VH region and a heavy chain constant region and a light chain comprising the VL region and a light chain constant region.

8. The isolated antibody or antigen-binding fragment thereof of claim 7, wherein heavy chain constant region is of the IgG isotype.

9. The isolated antibody or antigen-binding fragment thereof of claim 7, wherein the heavy chain constant region is an IgG1 constant region or an IgG4 constant region.

10. The isolated antibody of antigen-binding fragment thereof of claim 7, wherein the heavy chain constant region is Fc null.

11. The isolated antibody or antigen-binding fragment thereof of claim 9, wherein the heavy chain constant region is an IgG1 constant region and comprises at least one amino acid modification that reduces binding to one or more Fcgamma receptors.

12. The isolated antibody or antigen-binding fragment thereof of claim 9, wherein the heavy chain constant region is an IgG1 constant region and comprises: (i) one or more substitutions that reduce the binding affinity of the Fc domain to an Fc receptor, wherein at least one substitution is selected from E233P, L234V, L234A, L235A, L235E, G236A, G237A, E318A, K320A, K322A, A327G, A330S, and P331S, according to the EU index of Kabat numbering; and/or (ii) a GGGS (SEQ ID NO: 38) between G237 and G238 according to the EU index of Kabat numbering.

13. The isolated antibody or antigen-binding fragment thereof of claim 9, wherein the heavy chain constant region is an IgG1 constant region and comprises substitutions L234A and L235A according to the EU index of Kabat numbering.

14. The isolated antibody or antigen-binding fragment thereof or claim 13, wherein the heavy chain constant region comprises a substitution of P329 according to the EU index of Kabat numbering.

15. The isolated antibody or antigen-binding fragment thereof of claim 7, wherein the heavy chain comprises the amino acid sequence set forth in SEQ ID NO: 3.

16. The isolated antibody or antigen-binding fragment thereof of claim 15, wherein the light chain comprises the amino acid sequence set forth in SEQ ID NO:4.

17. The isolated antibody or antigen-binding fragment thereof of claim 14, wherein the light chain constant region is of the kappa isotype.

18. The isolated antibody or antigen-binding fragment thereof of claim 17, wherein the light chain comprises the amino acid sequence set forth in SEQ ID NO:4.

19. A pharmaceutical composition comprising the isolated antibody or antigen-binding fragment thereof of claim 5 and a pharmaceutically acceptable carrier.

* * * * *